United States Patent
Varona et al.

(10) Patent No.: US 6,838,154 B1
(45) Date of Patent: Jan. 4, 2005

(54) CREPED MATERIALS

(75) Inventors: Eugenio Go Varona, Marietta, GA (US); Monica Lynn Bontrager, Appleton, WI (US); Jaime Braverman, Atlanta, GA (US); Kuo-Shu Edward Chang, Roswell, GA (US); Michael Allen Daley, Alpharetta, GA (US); Karen Lynn English, Alpharetta, GA (US); Arthur Edward Garavaglia, Alpharetta, GA (US); Hristo Angelov Hristov, Roswell, GA (US); Nancy Donaldson Kollin, Roswell, GA (US); Tamara Lee Mace, Doraville, GA (US); David Michael Matela, Alpharetta, GA (US); Sharon Rymer, Neenah, WI (US); Reginald Smith, Roswell, GA (US); Roland Columbus Smith, Jr., Gainesville, GA (US); Michael Donald Sperl, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 686 days.

(21) Appl. No.: 09/209,044

(22) Filed: Dec. 9, 1998

Related U.S. Application Data

(63) Continuation-in-part of application No. 09/040,707, filed on Mar. 18, 1998, now Pat. No. 6,150,002, and a continuation-in-part of application No. 08/962,992, filed on Oct. 31, 1997, now Pat. No. 6,197,404.

(51) Int. Cl.$^7$ .......................... D06N 7/04; D04H 1/00; D04H 13/00; D04H 3/00; D04H 5/00; D04H 3/16; A61F 13/15; A61F 13/20

(52) U.S. Cl. ...................... 428/152; 442/340; 442/401; 604/358; 604/367; 604/368; 604/372

(58) Field of Search ................... 604/368, 358, 604/367, 372; 428/103, 152; 442/340, 401

(56) References Cited

U.S. PATENT DOCUMENTS

| 3,338,992 A | 8/1967 | Kinney | 264/24 |
| 3,341,394 A | 9/1967 | Kinney | 161/72 |

(List continued on next page.)

FOREIGN PATENT DOCUMENTS

| EP | 0 064 853 | 11/1982 | .......... D04H/1/54 |
| EP | 0 547 498 | 6/1993 | .......... A61F/13/15 |

(List continued on next page.)

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

(List continued on next page.)

*Primary Examiner*—Terrel Morris
*Assistant Examiner*—Christopher Pratt
(74) *Attorney, Agent, or Firm*—James B. Robinson

(57) ABSTRACT

There is provided a resilient, three dimensional material having fibrous texture and appearance and capable of fluid handling. It consists of a top surface and a bottom surface wherein fiber-like elements typically extend from one surface to the other forming flat to undulating surfaces characterized by a multiplicity of interconnected fluid passageways. Deformed, discontinuous film-like or encapsulated regions connect fiber-like elements and stabilize the material. The material of this invention is unique based on the three principle characteristics which are communicated in this application: 1) $f_r(\psi)<0.87$, 2) SA/VV<186 cm$^2$/cm$^3$, and 3) caliper<0.150 inches. This material is useful for a number of purposes, such as for use as a liner for personal care products like diapers, absorbent underpants, swim wear, feminine hygiene products, adult incontinence products and the like. The properties of the material may be tailored within the ranges of this invention to deliver optimal material performance for use in specific personal care products.

31 Claims, 14 Drawing Sheets

U.S. PATENT DOCUMENTS

| | | | |
|---|---|---|---|
| 3,502,763 A | 3/1970 | Hartmann | 264/210 |
| 3,542,615 A | 11/1970 | Dobo et al. | 156/181 |
| 3,668,054 A | 6/1972 | Stumpf | 161/128 |
| 3,687,754 A | 8/1972 | Stumpf | 156/72 |
| 3,692,618 A | 9/1972 | Dorschner et al. | 161/72 |
| 3,694,867 A | 10/1972 | Stumpf | 24/204 |
| 3,705,065 A | 12/1972 | Stumpf | 156/72 |
| 3,720,554 A | 3/1973 | Stumpf | 156/62.6 |
| 3,802,817 A | 4/1974 | Matsuki et al. | 425/66 |
| 3,849,241 A | 11/1974 | Butin et al. | 161/169 |
| 3,855,046 A | 12/1974 | Hansen et al. | 161/150 |
| 3,879,257 A | 4/1975 | Gentile et al. | 162/112 |
| 3,929,135 A | 12/1975 | Thompson | 128/287 |
| 4,063,995 A * | 12/1977 | Grossman | 162/112 |
| 4,158,594 A | 6/1979 | Becker et al. | 162/112 |
| 4,340,563 A | 7/1982 | Appel et al. | 264/518 |
| 4,374,888 A | 2/1983 | Bornslaeger | 428/198 |
| 4,631,933 A | 12/1986 | Carey, Jr. | 66/192 |
| 4,810,556 A * | 3/1989 | Kobayashi et al. | 428/152 |
| 4,891,957 A | 1/1990 | Strack et al. | 66/192 |
| 4,892,557 A | 1/1990 | Conklin et al. | 8/497 |
| 5,037,409 A | 8/1991 | Chen et al. | 604/358 |
| 5,057,368 A | 10/1991 | Largman et al. | 428/397 |
| 5,069,970 A | 12/1991 | Largman et al. | 428/373 |
| 5,102,724 A | 4/1992 | Okawahara et al. | 428/224 |
| 5,108,820 A | 4/1992 | Kaneko et al. | 428/198 |
| 5,108,827 A | 4/1992 | Gessner | 428/219 |
| 5,262,107 A | 11/1993 | Hovis et al. | 264/145 |
| 5,270,107 A | 12/1993 | Gessner | 428/296 |
| 5,277,976 A | 1/1994 | Hogle et al. | 428/397 |
| 5,298,315 A | 3/1994 | Fukui et al. | 428/298 |
| 5,336,552 A | 8/1994 | Strack et al. | 428/224 |
| 5,382,400 A | 1/1995 | Pike et al. | 264/168 |
| 5,466,410 A | 11/1995 | Hills | 264/172.11 |
| 5,543,202 A | 8/1996 | Clark et al. | 428/154 |
| 5,587,225 A | 12/1996 | Griesbach et al. | 428/198 |
| 5,591,149 A | 1/1997 | Cree et al. | 604/378 |
| 5,593,399 A | 1/1997 | Tanzer et al. | 604/368 |
| 5,601,542 A | 2/1997 | Melius et al. | 604/368 |
| 5,602,209 A * | 2/1997 | Warchol et al. | 525/410 |
| 5,614,281 A | 3/1997 | Jackson et al. | 428/100 |
| 5,623,888 A | 4/1997 | Zafiroglu | 112/414 |
| 5,649,919 A | 7/1997 | Roessler et al. | |
| 5,658,268 A | 8/1997 | Johns et al. | 604/361 |
| 5,669,900 A | 9/1997 | Bullwinkel et al. | 604/391 |
| 5,679,042 A | 10/1997 | Varona | 442/347 |
| 5,770,531 A | 6/1998 | Sudduth et al. | 442/361 |
| 5,846,232 A | 12/1998 | Serbiak et al. | 604/385.2 |

FOREIGN PATENT DOCUMENTS

| | | | |
|---|---|---|---|
| EP | 0 640 708 | 3/1995 | D04H/1/44 |
| EP | 0 672 774 | 9/1995 | |
| EP | 0 586 924 | 10/1997 | D04H/1/54 |
| EP | 0 858 790 | 2/1998 | A61F/13/00 |
| WO | 96/07384 | 3/1996 | A61F/13/46 |
| WO | 97/19808 | 6/1997 | B32B/5/02 |
| WO | 98/36721 | 8/1998 | A61F/13/15 |

OTHER PUBLICATIONS

Burgeni and Kapur, Textile Research Journal, vol. 37, pp. 356–366 (1967).

R. E. Mark, "*Handbook of Physical and Mechanical Testing of Paper and Paperboard*", Marcel Dekker Publ., 2, 283 (1984).

H. Kawai, S. Nomura, "*Developments in Polymer Characterization*", J. V. Dawkins, ed., Allied Science Publ., 4, 211 (1983).

J. J. Hermans, P. H. Hermans, D. Vermaas, A. Weideinger in *Rec. Trans. Chim.*, 65, 427 (1946).

"A refined method to evaluate diapers for effectiveness in reducing skin hydration using the adult forearm"; Frank J. Akin, Jac T. Lemmen, Dena L. Bozarth, Martin J. Garofalo and Gary L. Grove; Skin Research and Technology 1997; 3; 173–176.

* cited by examiner

CREPED MATERIALS

This application is a continuation-in-part of U.S. patent application Ser. No. 08/962,992 filed Oct. 31, 1997 now U.S. Pat. No. 6,197,404 and of U.S. patent application 09/040,707, filed Mar. 18, 1998 now U.S. Pat. No. 6,150,002.

This application is being filed the same day as a co-assigned case having attorney docket number 13493, entitled "Multi-Layer Liners for Personal Care Products".

FIELD OF THE INVENTION

The present invention relates to a material which may be used, for example, as a liner for personal care products like diapers, training pants, swim wear, absorbent underpants, adult incontinence products, bandages and feminine hygiene products.

BACKGROUND OF THE INVENTION

Personal care articles, such as infant and feminine care products are typically composed of multiple components including the cover (also known as topsheet or liner), absorbent layer(s) and baffle. The topsheet in conjunction with the absorbent layer(s) must deliver softness and comfort, protection, good absorbency and liquid intake properties, dryness, visual distinctiveness and cleanliness. The extent to which these traits are met is dependent on the interaction of a bodily fluid with the structure and surface chemistry of the cover and absorbent as well as the interface between adjacent or interconnected materials.

Two cover approaches have typically been pursued to attain the desired features: apertured film covers and nonwoven covers. Nonwoven materials are soft and comfortable but often lack the required functional attributes (clean, dry, and absorbent) while apertured film covers can deliver the required functionality but are generally hot, plasticky, and uncomfortable.

A number of apertured film covers have been described in the patent art. These vary widely in their functional performance. Several main categories of film covers are known based on their structure and the methods of manufacture. For instance, two dimensional film covers (using a slit and stretch aperture method) were developed by Hovis et al. (U.S. Pat. No. 5,262,107). Due to their structure, these apertured films have relatively slow intake rates and high rewet and staining compared to other apertured films. Three dimensional apertured film covers were described by Thompson et. al. (U.S. Pat. No. 3,929,135) and others using both vacuum aperturing and pin aperturing. These materials have relatively rapid intake, low rewet, and low staining due to their tailored structure including apertures on the top and bottom surface, depth of aperturing, and tapering of the apertures. Other structures have been created which have some characteristics of both two and three dimensional cover materials. These are often characterized as two dimensional films with appendages or extensions protruding from the bottom surface. They often are produced using pin aperturing techniques.

Nonwovens such as monocomponent spunbond webs often have poor functional performance due to their generally small average pore size, low permeability, and two dimensional nature. Other structures such as crimped conjugate spunbond webs and through air bonded carded webs can be three dimensional but also tend to have low permeability and small average pore size. The permeability and pore size may be increased through, for example, increased fiber denier and decreased basis weight, but at the extreme limits, softness and other aesthetic features can be compromised. Additionally, under these conditions one often sees a tradeoff in properties; for example, such than intake rate increases with increase in permeability, but rewet and staining may also increase.

Integrated composite structures are also described in the art and include apertured film/nonwoven laminates and nonwoven/nonwoven laminates. These structures often deliver improvements in functional performance and softness, however, these structures are often more expensive due to their increased complexity and the incorporation of multiple layers of materials.

The cover is sometimes referred to as a body side liner or topsheet when referring to diapers, and is usually adjacent a surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

A properly functioning diaper body side liner should have good intake properties so that the incoming liquid stream is transported through the material completely and hence, minimal pooling and spreading of the liquid at the surface occurs. Pooling and spreading at the surface can contribute to leakage and increase skin hydration or wetness. Additionally, the body side surface of the liner should have minimal saturation so that skin hydration does not increase. It is desirable that personal care articles be designed so as to minimize skin hydration since its believed to contribute to the occurrence of diaper rash. If the liner has poor liquid intake qualities and remains saturated, or has fluid spreading properties, skin hydration will be increased.

There remains a need for a material which delivers the desired functional attributes of cleanliness, dryness and absorbency in one material, while still maintaining the softness and comfort normally associated with fibrous nonwoven webs. It is one object of this invention to provide such a material.

SUMMARY OF THE INVENTION

The object of the invention is a resilient, three dimensional material having fibrous texture and appearance and capable of fluid handling. It has a top surface and a bottom surface and fiber-like elements can extend from one surface to the other, forming flat to undulating surfaces characterized by a multiplicity of interconnected fluid passageways. Deformed, discontinuous film-like or encapsulated regions connect fiber-like elements and stabilize the material. The material of this invention is unique based on the three principle characteristics which are: 1) $f_j(\psi)<0.87$, 2) $SA/VV<186$ $cm^2/cm^3$, and 3) caliper<0.150 inches. This material is useful for a number of purposes, such as for use as a liner for personal care products like diapers, absorbent underpants, swim wear, feminine hygiene products, adult incontinence products and the like. The properties of the material may be tailored within the ranges of this invention to deliver optimal material performance for use in specific personal care products.

BRIEF DESCRIPTION OF THE DRAWINGS

FIG. 8a represents a fabric having fiber orientation in the Z direction. FIG. 8b represents a fabric having fiber orientation in the Y direction. FIG. 8c represents a fabric having a random fiber orientation.

DEFINITIONS

Figure 1:
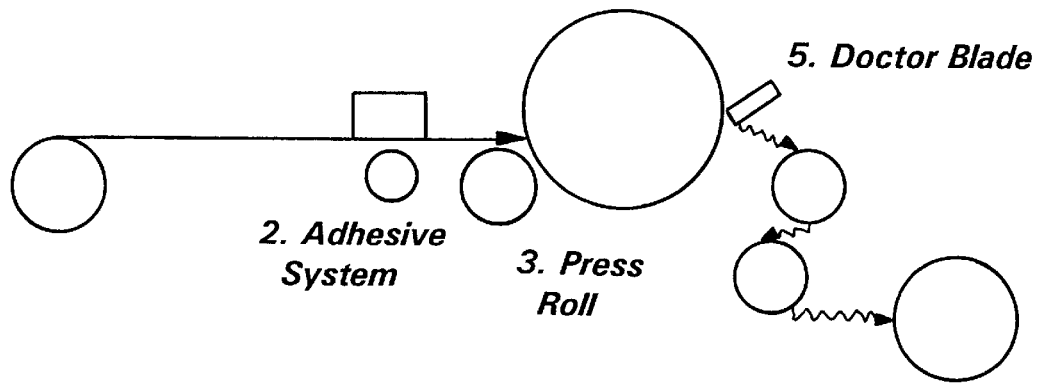
FIG. 1 shows a diagram of a process for creping a web.

"Disposable" includes being disposed of after a single use and not intended to be washed and reused.

"Front" and "back" are used throughout this description to designate relationships relative to the garment itself, rather than to suggest any position the garment assumes when it is positioned on a wearer.

"Inward" and "outward" refer to positions relative to the center of an absorbent garment, and particularly transversely and/or longitudinally closer to or away from the longitudinal and transverse center of the absorbent garment.

"Liquid" means a substance and/or material that flows and can assume the interior shape of a container into which it is poured or placed. It is meant to include but not be limited to bodily exudates, menstrual discharge, menses, urine, blood, and runny bowel movement.

"Liquid communication" means that liquid is able to travel from one layer to another layer, or one location to another within a layer.

"Longitudinal" and "transverse" have their customary meaning. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the fiber's polymer density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.91 g/cc and multiplying by 0.00707. Thus, a 15 micron polypropylene fiber has a denier of about 1.45 ($15^2 \times 0.91 \times 0.00707 = 1.45$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in US Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 30 microns. The fibers may also have shapes such as those described in U.S. Pat. Nos. 5,277,976 to Hogle et al., U.S. Pat. Nos. 5,466,410 to Hills and 5,069,970 and 5,057,368 to Largman et al., which describe fibers with unconventional shapes. As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

"Conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook Polymer Blends and Composites by John A. Manson and Leslie H. Sperling, copyright 1976 by Plenum Press, a division of Plenum Publishing Corporation of New York, IBSN 0-306-30831-2, at pages 273 through 277. "Personal care product" means diapers, training pants, swim wear, absorbent underpants, adult incontinence products, bandages and feminine hygiene products.

"Feminine hygiene products" means sanitary napkins or pads, tampons and panty-liners.

"Target area" refers to the area or position on a personal care product where an insult is normally delivered by a wearer.

"Absorbent articles" refers to materials which when used independently or in conjunction with other materials are capable of fluid intake, absorption, or permeation of fluid into void spaces.

TEST METHODS AND MATERIALS

Density (Test Method A)

The density of a material is calculated by dividing the weight per unit area of a sample in grams per square meter (gsm) by the material caliper. A total of five samples would be evaluated and averaged for the density values. Density is usually reported in units of grams/cubic centimeter (g/cc) and symbolized by Greek letter $\rho$.

Pore Size Measurements (Test Method B)

Figure 2:
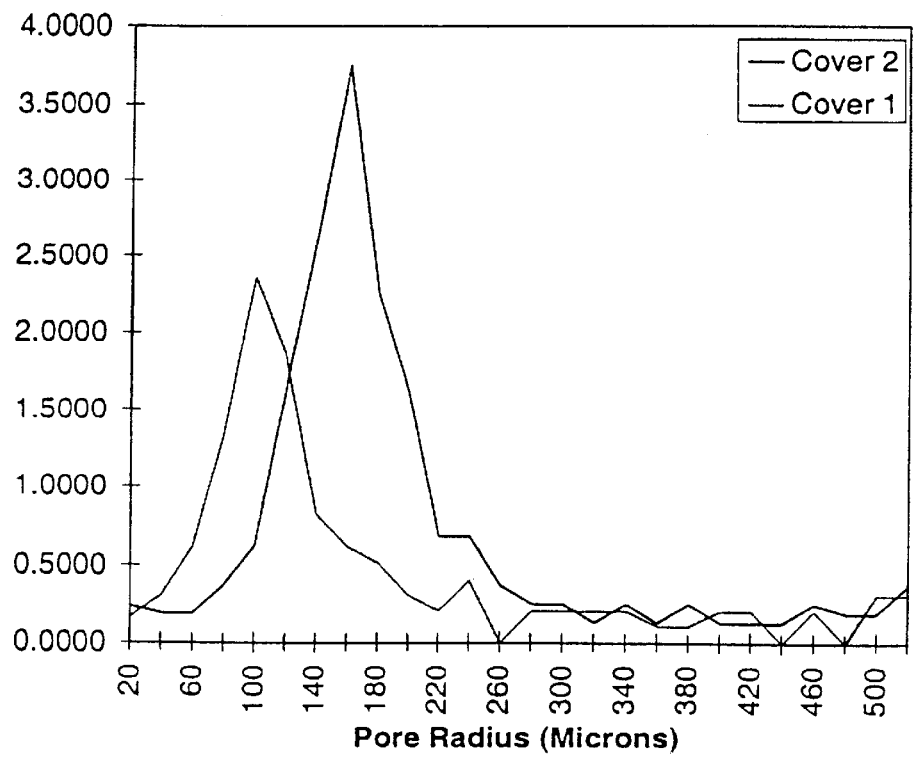
FIG. 2 is a graph of pore size distribution of a web.

A pore radius distribution chart as illustrated in FIG. 2 shows pore radius in microns in the x-axis and pore volume (volume absorbed in cc of liquid/gram of dry sample at that pore interval) in the y-axis. This is determined by using an apparatus based on the porous plate method first reported by Burgeni and Kapur in the Textile Research Journal Volume 37, pp 356-366 (1967). The system is a modified version of the porous plate method and consists of a movable Velmex stage interfaced with a programmable stepper motor and an electronic balance controlled by a computer. A control program automatically moves the stage to the desired height, collects data at a specified sampling rate until equilibrium is reached, and then moves to the next calculated height. Controllable parameters of the method include sampling rates, criteria for equilibrium and the number of absorption/desorption cycles.

Data for this analysis was collected using mineral oil (Peneteck Technical Mineral Oil with a viscosity of 6 centipoise Manufactured by Penreco of Los Angeles, Calif. in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. This method is described in more detail in U.S. Pat. No. 5,679,042 to Varona.

Permeability (Test Method C)

Permeability is obtained from a measurement of the resistance by the material to the flow of liquid. A liquid of known viscosity is forced through the material of a given thickness at a constant flow rate and the resistance to flow, measured as a pressure drop is monitored. Darcy's Law is used to determine permeability as follows:

Permeability=flow rate×thickness×viscosity/pressure drop Equation(1) where the units are:

| permeability: | $cm^2$ or darcy | 1 darcy = $9.87 \times 10^{-9}$ $cm^2$ |
|---|---|---|
| flow rate: | cm/sec | |
| viscosity: | pascal-sec | |
| pressure drop: | pascals | |

The apparatus consists of an arrangement wherein a piston within a cylinder pushes liquid through the sample to be measured. The sample is clamped between two aluminum cylinders with the cylinders oriented vertically. Both cylinders have an outside diameter of 3.5", an inside diameter of 2.5" and a length of about 6". The 3" diameter web sample is held in place by its outer edges and hence is completely contained within the apparatus. The bottom cylinder has a piston that is capable of moving vertically within the cylinder at a constant velocity and is connected to a pressure transducer that capable of monitoring the pressure of encountered by a column of liquid supported by the piston. The transducer is positioned to travel with the piston such that there is no additional pressure measured until the liquid column contacts the sample and is pushed through it. At this point, the additional pressure measured is due to the resistance of the material to liquid flow through it.

The piston is moved by a slide assembly that is driven by a stepper motor. The test starts by moving the piston at a constant velocity until the liquid is pushed through the sample. The piston is then halted and the baseline pressure is noted. This corrects for sample buoyancy effects. The movement is then resumed for a time adequate to measure the new pressure. The difference between the two pressures is the pressure due to the resistance of the material to liquid flow and is the pressure drop used in Equation(1). The velocity of the piston is the flow rate. Any liquid whose viscosity is known can be used, although a liquid that wets the material is preferred since this ensures that saturated flow is achieved. The measurements were carried out using a piston velocity of 20 cm/min, mineral oil (Peneteck Technical Mineral Oil manufactured by Penreco of Los Angeles, Calif.) of a viscosity of 6 centipois.

Alternatively, permeability can be calculated from the following equation:

$$\text{Permeability}=0.051*R*(1-\text{Porosity})*(\text{Porosity}/(1-\text{Porosity}))^{2.75} \quad \text{Equation(2)}$$

where $R$=fiber radius $$\text{and Porosity}=1-(\text{web density}/\text{fiber density}) \quad \text{Equation(3)}$$

Reference for Equation(2) can be found in the article "Quantification of Unidirectional Fiber Bed Permeability by J. Westhuizen and J. P. Du Plessis in the Journal of Composite Materials, 28(7), 1994. Note that the equations show that permeability can be determined if fiber radius, web density and fiber density are known.

Conductance: This is calculated as permeability per unit thickness and gives a measure of the openness of a particular structure and so an indication of the relative ease at which a material will pass liquid. The units are darcies/mil.

Material Caliper (Thickness) (Test Method D)

The caliper of a material is a measure of thickness and is measured at 0.05 psi with a Starret-type bulk tester, in units of millimeters or inches. The foot of the bulk tester used in these studies is a small acrylic cylinder measuring 3" wide by 0.5 inches in thickness. In practice, 10 repetitions of any measurement should be made.

Absorbency Test or Rate Block Intake Test (Test Method E)

Figure 25:
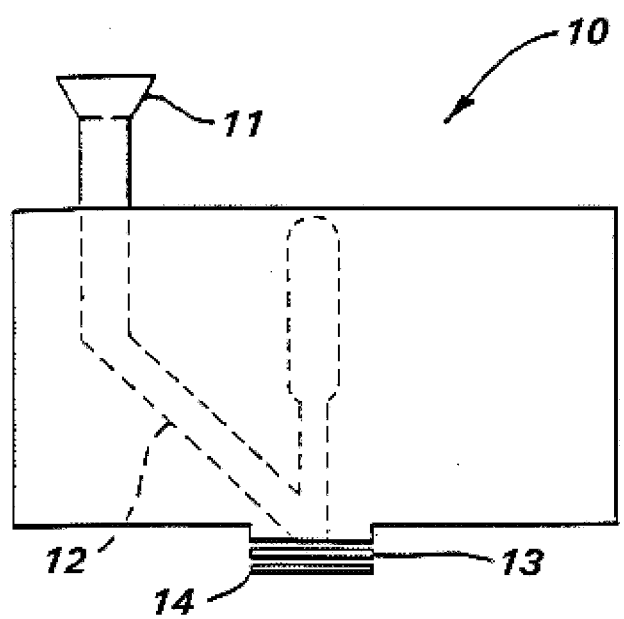
FIG. 25 is a rate block for use in intake time testing of materials.

This test is used to determine the intake time of a known quantity of fluid into a material and/or material system. The test apparatus consists of a rate block as shown in FIG. 25, and a timer or stopwatch. A 4 inch by 4 inch (102 mm by 102 mm) piece of absorbent 14 and cover 13 were die cut. The specific covers to be tested are described in the specific examples. The absorbent used for these studies consisted of a 250 gsm airlaid made of 90% Coosa 0054 pulp and 10% Hoechst-Celanese T-255 conjugate binder fiber and the density for this absorbent was 0.10 g/cc. The sample cover 13 to be tested was placed over the absorbent 14 and the rate block 10 was placed on top of the two materials. For our work, 2 ml of an artificial menses fluid as prepared below was delivered into the test apparatus funnel 11 and a timer was initiated. The fluid moved from the funnel 11 into a capillary 12 where it was delivered to the material or material system. The timer was stopped when all the fluid was absorbed into the material or material system as observed from the chamber in the test apparatus. The intake time for a known quantity of test fluid was recorded for a given material or material system. This value is a measure of a material or materials systems absorbency with lower intake time representing "more absorbent" materials or systems. Five to ten repetitions were performed to determine average intake time.

Rewet Test (Test Method F)

This test is used to determine the amount of fluid that will come back to the surface of a cover when a load is applied. The amount of fluid that comes back through the surface is called the rewet value. The more fluid that comes to the surface the larger the rewet value while the smaller the amount of fluid that comes back to the surface the lower the rewet value. Lower rewet values are associated with a dryer material and hence a dryer product. In considering rewet, three properties are important:

1) intake, if the material/system does not have good intake then fluid can rewet,
2) ability of absorbent to hold fluid, the more the absorbent holds onto the fluid the less is available for rewet, and
3) flowback, the more the cover prohibits fluid from coming back through the cover the lower the rewet.

In the testing herein, a cover system is being evaluated so the absorbent is kept constant. The absorbent is a 250 gsm airlaid material made of 90% Coosa 0054 pulp and 10% HC T-255 binder with a density of 0.10 g/cc. Two ml of artificial menses fluid are insulted into the rate block apparatus and allowed to absorb into a 4"×4" sample of the cover material which is placed on top of a 4"×4" absorbent piece. The fluid is allowed to interact with the system for 1 minute as the rate block rests on top of the materials. The material system (cover and absorbent) is placed onto a closed bag, partially filled with saline solution. The fluid bag was positioned on top of a lab jack. Pieces of blotter paper are weighed and placed on top of the material system. The bag with the material system is raised against a fixed acrylic plate using the lab jack until a total of 1 psi is applied. The pressure is held fixed for 3 minutes after which the pressure is removed and the blotter paper is weighed. The blotter paper should retain any fluid that was transferred to it from the cover/absorbent system. The difference in weight between the original blotter and the blotter after the absorption experiment is the rewet value.

Staining/Fluid Retention Test (Test Method G)

This test enables the stain size, intensity, and fluid retention in components to be observed with fluid flow rate and pressure. A materials system (cover and absorbent core) measuring 4"×4" was placed beneath an acrylic plate having a ⅛" (3 mm) diameter hole bored into the center. A piece of ⅛" tubing was connected to the hole with a fitting. The absorbent piece consisted of a 250 gsm airlaid made of 90% Coosa 0054 pulp and 10% HC T-255 binder. The total density for the absorbent was 0.10 g/cc. Artificial menses fluid was delivered to the sample using a syringe pump at a specified rate and for a specified volume. In these experiments, the pump was programmed to deliver a total volume of 1 ml to the samples where the samples were under pressures of 0 psi, 0.008 psi, and 0.8 psi. These pressures were applied using a weight which was placed on top of the acrylic plates and distributed evenly. The flow rate of the pump was programmed to deliver at rates of 1 ml/sec. The stain size (area) for the cover materials was measured manually and the amount of fluid in each component of the system was measured by weight before and after absorption of the fluid. The stain intensity was evaluated qualitatively by comparison of samples. Staining information could also be recorded using a digital camera and could be further analyzed with standard image analysis. Fluid retention was measured by weighing the cover before and after fluid insult. Average stain size and fluid retention were determined from at least five repetitions at each pressure.

Fiber Orientation in Polypropylene Spunbonds and Creped Spunbonds via Two-dimensional Wide Angle X-ray Scattering (Test Method H)

In a variety of materials, such as spunbond and meltblown fabrics, papers, airlaid materials and others, the control of the fiber orientation distribution is an important task.

A number of physical properties of the final product, such as machine- and cross-direction (MD and CD) strength, porosity and loft, depend on the overall fiber orientation. The fiber orientation may affect some other attributes of the product such as aesthetics, cloth-like appearance and ultimately customer satisfaction.

Depending on the manufacturing process, the fiber orientation in polypropylene (PP) spunbond fabrics can vary considerably. Quantitative analysis of the fiber orientation in fibrous materials is performed with the help of the "fiber orientation distribution function" (f-ODF) (see R. E. Mark, in "Handbook of Physical and Mechanical Testing of Paper and Paperboard", Marcel Dekker Publ., 2, 283 (1984)). In the most general case it is a three-dimensional (3-D) function. To obtain the complete f-ODF a variety of experimental methods have been proposed (see R. E. Mark, in "Handbook of Physical and Mechanical Testing of Paper and Paperboard" Marcel Dekker Publ., 2, 283 (1984)) and H. Kawai, S. Nomura, in "Developments in Polymer Characterization", J. V. Dawkins, ed., Allied Science Publ., 4, 211 (1983)). Most frequently used techniques include mechanical and optical methods, electron microscopy and X-ray diffraction. The mechanical methods are simple to use, but the agreement with more direct methods is generally not very good. A very detailed picture of the fiber orientation can be obtained by using microscopy methods, however their application as a rule requires extensive sample preparation, frequently is tedious and time consuming. In contrast the X-ray methods require little sample preparation, and in the case of semicrystalline fibers (which is the case with PP) the ODF can be obtained in a relatively short time. This is further simplified if one is interested in the average fiber orientation with respect to a chosen direction rather than the complete (3-D) ODF.

The method herein works well for polypropylene which crystallizes in its stable form ($\alpha$-form crystals, monoclinic) with the c-crystal axis along the fiber axis. After minor modifications, this method can be applied for other PP crystalline forms and other types of semicrystalline polymeric and nonpolymeric fibers. The applicability of the method is demonstrated on a series of creped PP spunbonds.

Crystalline Orientation in a Single Polypropylene Fiber

Figure 9:
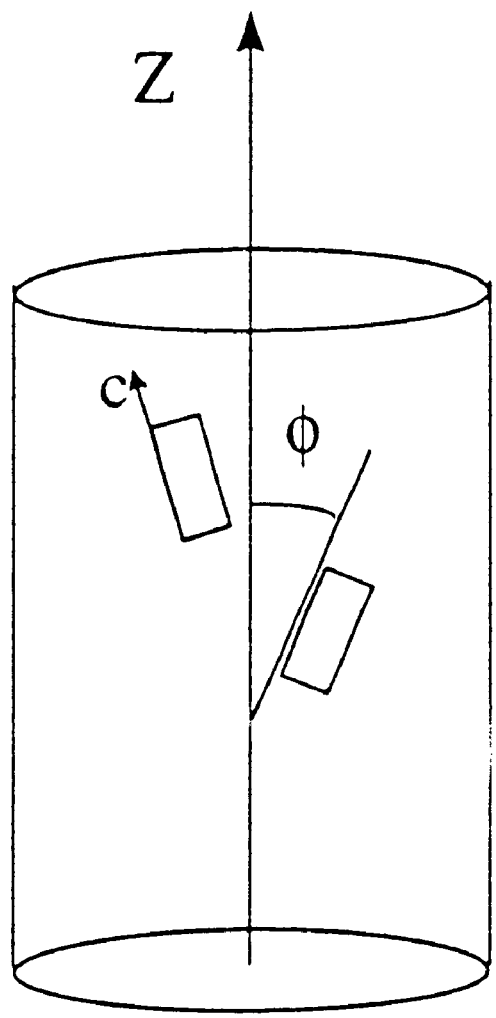
FIG. 9 is a representation of a cylinder having a Z axis along the centerline of its length and angles phi and c relative to the axis.
Figure 10:
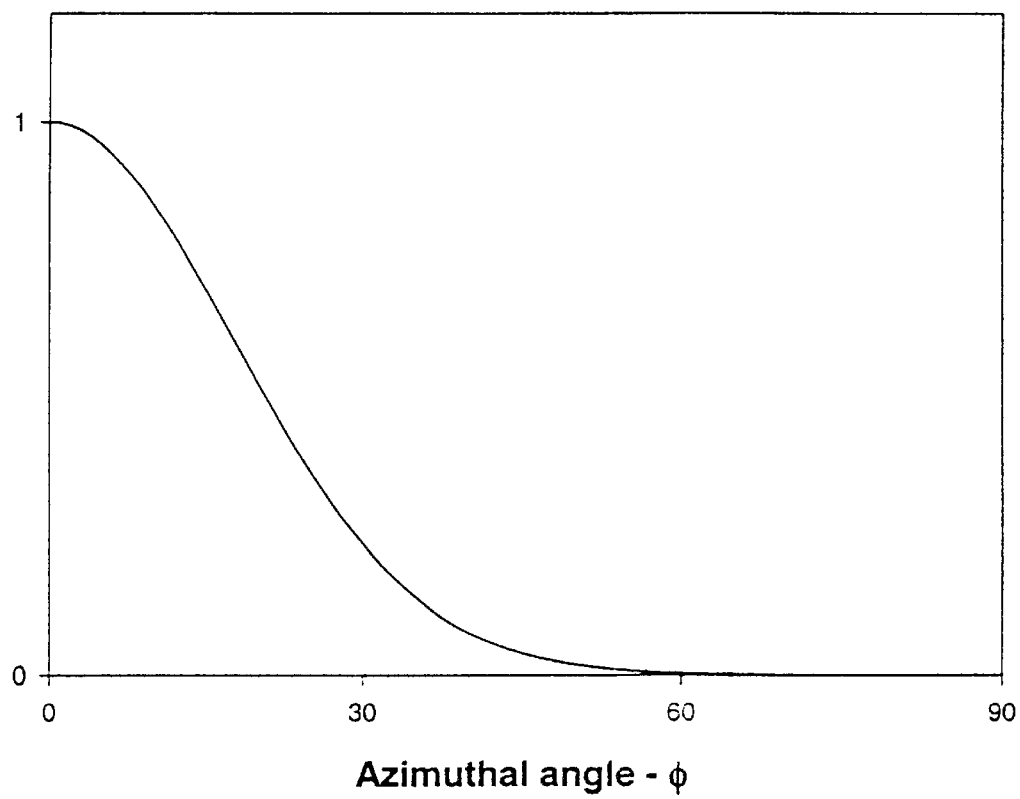
FIG. 10 is a graph of ODF-I($\phi$) on the y-axis versus azimuthal angle $\phi$ on the x-axis.

In a PP fiber containing $\alpha$-form crystals exhibiting c-axis orientation, the crystalline orientation with respect to the fiber axis is derived from the crystalline orientation distribution function (c-ODF). Assuming that the fiber is aligned along one of the main axes of reference (axis OZ in FIG. 9) and taking into account the cylindrical symmetry with respect to the fiber axis, the c-ODF in the real space (or r space) is proportional to the number of crystals having specific orientation. The c-ODF in the diffraction space (or k space) coincides with the azimuthal X-ray intensity distribution from a set of planes perpendicular to axis OZ for perfectly aligned crystals. (For the simplest possible case of cubic crystals, (00l) planes are most convenient for this purpose.) The shape of such distribution is shown schematically in FIG. 10. After proper normalization the value of the ODF at angle $\phi$ is proportional to the number of the specified crystallographic planes having angles ($\pi/2$-$\phi$) with the fiber axis. Since the size of the crystals does not vary considerably for given production conditions, i. e. the number of planes per crystallite is relatively constant, the c-ODF is proportional to the number of crystallites having specific orientation. It is important to note that the normalized c-ODF can be interpreted, also, as the probability of finding a certain portion of crystals with specific orientation (see H. Kawai, S. Nomura, in "Developments in Polymer Characterization", J. V. Dawkins, ed., Allied Science Publ., 4, 211 (1983)). A quantitative measure of the average orientation of the crystalline phase is the Herman's orientation factor (see J. J. Hermans, P. H. Hermans, D. Vermaas, A. Weidinger in Rec. Trans. Chim., 65, 427 (1946)):

$$i\ f_H = (3\langle\cos^2\phi\rangle - 1)/2 \qquad \text{Equation(4)}$$

where $$\langle\cos^2\phi\rangle = \frac{\int_0^{\pi/2} I(\phi)\cos^2\phi\sin\phi\,d\phi}{\int_0^{\pi/2} I(\phi)\sin\phi\,d\phi} \qquad \text{Equation(5)}$$

and $\phi$ or $\phi_{c,z}$ is the angle between the crystallographic c-axis and the fiber axis. The Herman's orientation factor has a value of 1 for perfectly aligned crystals, 0 for random orientation and $-0.5$ for crystals oriented perpendicularly to the axis of reference. In practice the crystalline orientation in z-aligned PP fibers is computed:

$$\langle\cos^2\phi_{c,z}\rangle = 1 - 1.099\langle\cos^2\phi_{110,z}\rangle - 0.901\langle\cos^2\phi_{040,z}\rangle \qquad \text{Equation(6)}$$

where $\phi_{110,z}$ is the angle between the normal to (110) crystallographic planes and the fiber axis, $\phi_{040,z}$ is the angle between the normal to (040) crystallographic planes and the fiber axis. The coefficients 1.099 and 0.901 reflect the monoclinic symmetry of the crystal.

Figure 11:
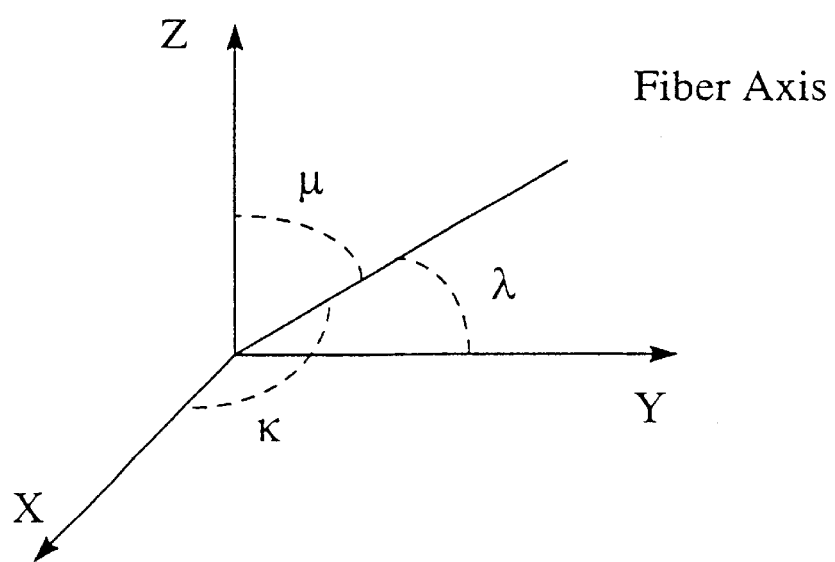
FIG. 11 is a diagram of a fiber axis versus three axes, X, Y and Z. Between the fiber and Z is angle $\mu$, between the fiber and Y is the angle X, and between the fiber an X is the angle κ.

In the most general case of a specimen oriented arbitrary in space, the crystalline orientation needs to be determined from the complete stereographic (i. e. 3-D) analysis. In the studies of textures in wires and sheet materials, the streographic projections of the c-ODF on specified sample planes are known as "pole figures". As indicated in the introduction we are interested in the average orientation, rather than the complete ODF. Instead of constructing the pole figures the following approach will be used:

From the 3-D c-ODF, the averaged spatial orientation can be computed with the aid of a set of equations similar to equations (4) and (5) and the Euler angles $\kappa$, $\lambda$ and $\mu$ as shown in FIG. 11. Similarly to equation (4) one can define three orientation factors:

$$i\ f_{HX} = (3\langle\cos^2\kappa\rangle - 1)/2$$

$$i\ f_{HY} = (3\langle\cos^2\lambda\rangle - 1)/2$$

$$i\ f_{HZ} = (3\langle\cos^2\mu\rangle - 1)/2 \qquad \text{Equations(7)}$$

where the averaged squares of the cosines are computed from equation (5) by substituting $\phi$ with the respective angle. Taking into account that:

$$\cos^2\kappa + \cos^2\mu + \cos^2\mu = 1 \qquad \text{Equation(8)}$$

it can be shown that the following is true for any set of values of the Euler's angles:

$$i\ f_{HX}+f_{HY}+f_{HZ}=0 \quad \text{Equation(9)}$$

Equations (5) and (6) indicate that if one knows two of the orientation factors the third one can be easily computed, thus the crystalline orientation factor with respect to any axis of reference can be determined.

Figure 12:
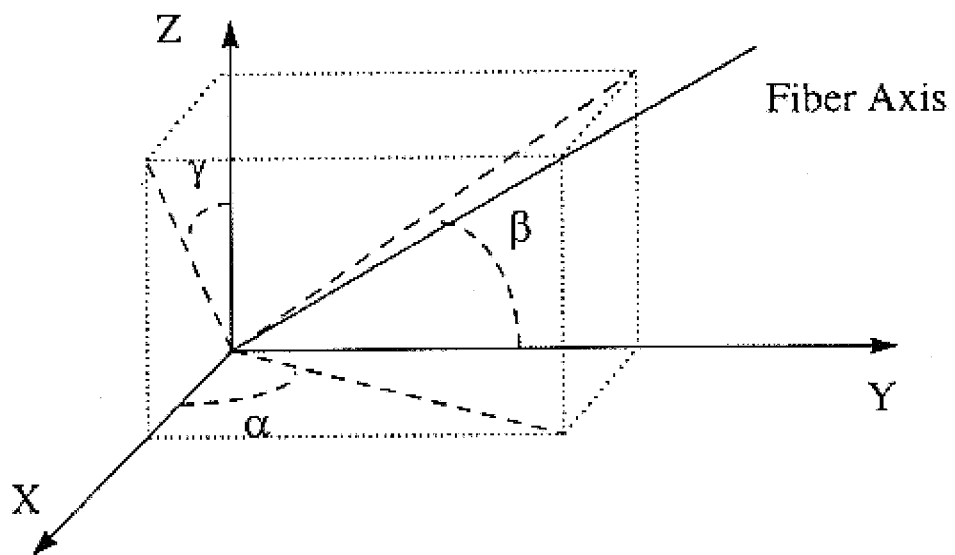
FIG. 12 is the projection of the Euler angles α, β and γ on the coordinate planes.

It is often much easier to obtain the experimental X-ray intensity distributions in some of the coordinate planes (XOY, XOZ, or YOZ) rather than the 3-D intensity distribution. In FIG. 12 are shown the projections of the Euler's angles (labeled α,β and γ) on the coordinate planes. Geometrical considerations show that in this case instead of equation (5) the following relationship holds true:

$$i\ tg\alpha \times tg\beta \times tg\gamma = 1 \quad \text{Equations(10)}$$

Equation (10) demonstrates, that if the experimental intensity distribution in two mutually perpendicular planes is known, the orientation factors with respect to any of the coordinate axes can be derived. Similarly to equation (7) the orientation factors are written as:

$$i\ f_X = (3\langle\cos^2\alpha\rangle - 1)/2$$
$$f_Y = (3\langle\cos^2\beta\rangle - 1)/2 \quad \text{Equations(11)}$$
$$i\ f_Z = (3\langle\cos^2\gamma\rangle - 1)/2$$

It can be shown also that the averaged squares of the cosines of the Euler angles and their respective orientation factors can be computed from α, β and γ.

Fiber Orientation in a Spunbond (SB) Fabric

While there are many ways to define a fiber orientation distribution function, we will use the following approach:

Assume that the $i^{th}$ fiber in the SB fabric is divided into $p_i$ straight fiber segments with a constant length. The choice of this unit length is not critical as long as it is large enough, so each segment contains approximately the same number of crystallites, but small enough to follow closely the tortuous path of the fiber into the spunbond. Since the diameter of typical SB fibers is 10 μm or larger and the crystallite size is less than 100 Å, a unit length of the order of the fiber diameter is one appropriate choice. Let us further assume that $m_i$ segments ($m_i \leq p_i$) reside inside a unit solid angle $d\kappa d\lambda d\mu$ having Euler coordinates (κ,λ,μ). (FIG. 11). The sum:

$$S_m(\kappa, \lambda, \mu) = \sum_{i=1}^{n} m_i \quad \text{Equation(12)}$$

where n is the total number of fibers in the fabric, gives the total number of fiber segments aligned along direction in space with Eulerian coordinates (κ,λ,μ). The total number of fiber segments within the SB fabric is therefore:

$$S_p = \sum_{i=1}^{n} p_i \quad \text{Equations(13)}$$

The ratio of the two sums, which gives the relative number of chain segments aligned along direction in space (k,l,m) is the fiber orientation distribution function, i. e.:

$$f-ODF(\kappa, \lambda, \mu) = \frac{S_m(\kappa, \lambda, \mu)}{S_p} \quad \text{Equation(14)}$$

Equation (14) can be interpreted also as the probability of finding a certain portion of chain segments with specific orientation. Since the unit length is much smaller than the overall length of the fibers, the sums in (12)–(14) can be substituted by integrals when necessary. Since each chain segment contains the same number of crystallites, it is apparent that the f-ODF is correlated to the c-ODF.

As discussed above, to uniquely determine the averaged spatial orientation it is sufficient to determine the orientation distribution in two mutually perpendicular planes.

Figure 5:
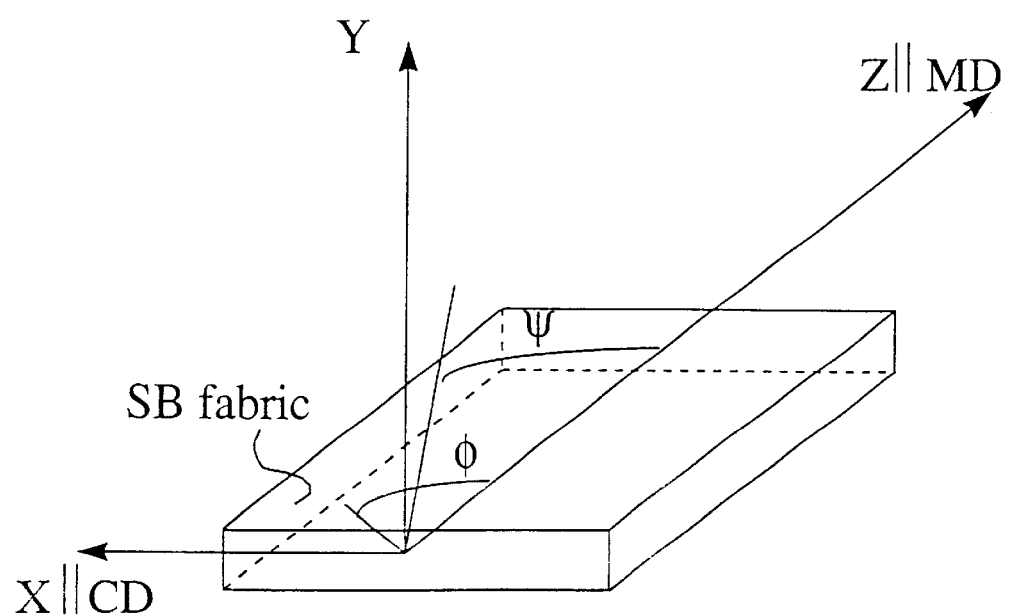
FIG. 5 is a representation of a fabric having X, Y and Z coordinates.

Fiber Orientation in the Plane of the Fabric (XOZ in FIG. 5)

The experimentally recorded azimuthal X-ray intensity distribution, from an appropriate set of crystallographic planes, of the SB fabric will depend on both, the c-ODF and the f-ODF. To continue further we will assume that the fiber orientation distribution and the crystalline orientation distribution in an "average" fiber are independent of each other. Keeping in mind the probabalistic interpretation of the orientation distribution, it is apparent, that in the r space the probability of finding a certain portion of crystals along a specified direction is given by the product of the two ODF's. Mathematically this dependence in the k space is expressed as a Fourier convolution:

$$i\ I_{SB}(\phi) = i\ I_c(\phi) \boxtimes I_f(\phi) \quad \text{Equation(15)}$$

where $I_{SB}(f)$ is the SB fabric experimental intensity, $I_c(\phi)$ is the crystalline X-ray intensity for a single fiber (see section I), $I_f(\phi)$ is the broadening resulting from orientation distribution of the fiber axes and the symbol indicates Fourier convolution. To compute the fiber orientation factor we need obtain $I_f(\phi)$, i. e. to solve equation (15) with respect to $I_f(\phi)$. The approach in deriving the fiber's orientation factor from experimental data will depend on the level of crystalline orientation.

a) Crystals perfectly aligned along the fiber axis (φ=0, $f_H$=1, please note that angle φ in FIG. 5 corresponds to angle γ in FIG. 12)

It can be shown that for perfect orientation the crystalline ODF is a Dirac δ function centered at the origin. It can be shown also that the Fourier convolution of a reasonably smooth function with a Dirac δ function gives the function itself. As a result the normalized X-ray intensity scattered at an azimuthal angle φ is directly proportional to the number of chain segments aligned in this direction. Thus the use of equations (4)-(7) directly gives the average orientation of the axes of the fiber segments. In this extreme case the experimentally measured $f_{\phi SB} = f_{\phi F}$. ($f_{\phi SB}$ is the in-plane orientation factor computed from the X-ray diffractograms of the fabric in transmission and $f_{\phi F}$ is the respective orientation factor of the fibers).

b) Nonperfect alignment of crystals

To obtain $I_f(\phi)$, we will use the Fourier convolution theorem stating that a convolution of two functions, is a product in the inverse space, i. e.:

$$\hat{I}_{SB}(\phi^*) = \hat{I}_c(\phi^*) \times \hat{I}_f(\phi^*) \quad \text{Equation(16)}$$

where φ*=φ is the azimuthal angle in the inverse space and $\hat{I}_x(\phi^*)$ are the Fourier transforms of the respective quantities from equation (15). It should be noted that the inverse of the diffraction space (or k space) is the real space (or r space) and vice versa. To derive the fiber ODF it is first necessary to record separately the experimental $I_c(\phi)$ and $I_{SB}(\phi)$, second execute the Fourier transformation and divide them:

$$\hat{I}_f(\phi^*) = \hat{I}_{SB}(\phi^*)/\hat{I}_c(\phi^*) \quad \text{Equation(17)}$$

$\hat{I}_f(\phi^*)$ is subsequently back transformed and the so obtained in-plane f-ODF (i. e. $I_f(\phi)$) can be used to compute the average orientation via equations (4)–(6).

Fiber Orientation in a Plane Perpendicular to the Plane of the Fabric (YOZ in FIG. 5)

All the relationships given in section II.1 (equations (15)–(17)) are applicable in this case, however angle $\phi$ needs to be replaced by angle $\psi$ (in FIG. 5, please note that angle $\psi$ in this figure corresponds to angle $(\pi/2-\beta)$ in FIG. 12).

While in practice it is very unlikely to have a material with $f_H=1$, very often the orientation of the crystalline phase within the fibers is much higher than the orientation of the fibers with respect to some characteristic directions. In such cases the direct use of equations (4)–(6) will not introduce substantial errors.

Since the Fourier transformation of a constant is a Dirac $\delta$ function, it is evident that the approach described herein is not applicable in the case of fibers exhibiting random crystalline orientation. However, this situation is almost never encountered in melt spun PP fibers.

Materials

The following materials were used in the present study:

A Control of approximately 3.5 dpf polypropylene fibers having about 8 weight percent AMPACET 41438 TiO2 concentrate as well as Cover 0, Cover 2, Cover 6 and Cover 7 (These covers are defined in Table 1).

Equipment and Experimental Procedures

The measurements were performed on Siemens GADDS diffractometer with a three circle goniometer, in Cu K$\alpha$ radiation. The diffracted intensity was recorded with a two dimensional (2-D) Hi-Star multiwire detector. The shape of the X-ray beam is circular with diameter 200 $\mu$, and the sample to detector distance was 60 mm.

To obtain the fibers ODF in the plane of the fabric, the 2-D intensities from all fabrics were recorded in transmission geometry. To determine the initial crystalline ODF, i. e. $I_c(\phi)$, a set of parallel fibers was fixed on a frame. This specimen was also studied in transmission geometry.

To obtain the fibers ODF in the plane perpendicular to the plane of the fabric, the materials were studied in reflection geometry, with the incident beam perpendicular to the machine direction. The angle between the incident beam and the plane of the sample ($\theta_o$) was chosen at 5°. Keeping in mind that for PP all the crystalline reflections are at 2$\theta$ angles larger than 10°, this choice is adequate.

Fiber Axis Distribution in the Plane of the Fabric (XOZ in FIG. 5)

Figure 13:
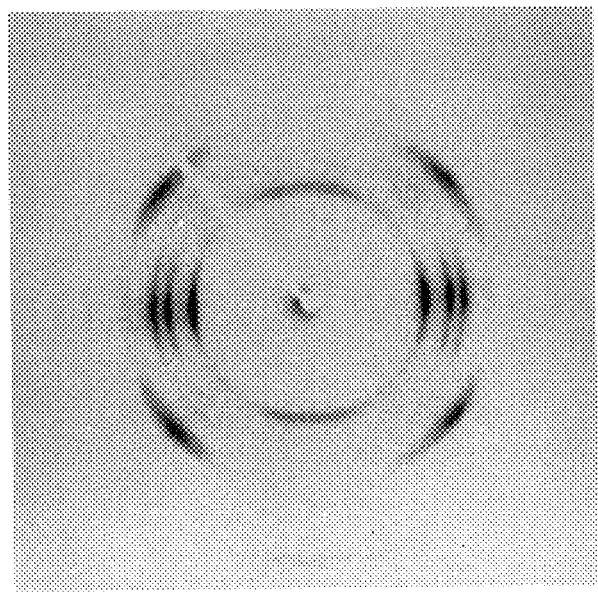
FIG. 13 is a 2-D X-ray intensity distribution, transmission geometry for specimen: Control, fiber axis vertical, X-ray perpendicular to the plane of the paper.
Figure 14:
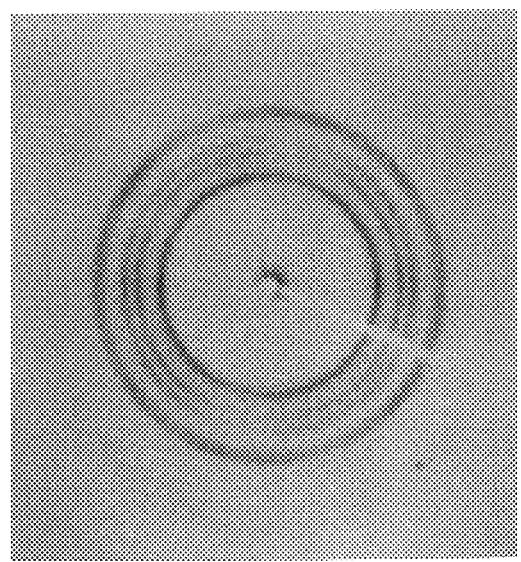
FIG. 14 is a 2-D X-ray intensity distribution, transmission geometry for specimen: Cover 0, MD vertical, X-ray perpendicular to the plane of the paper.
Figure 15:
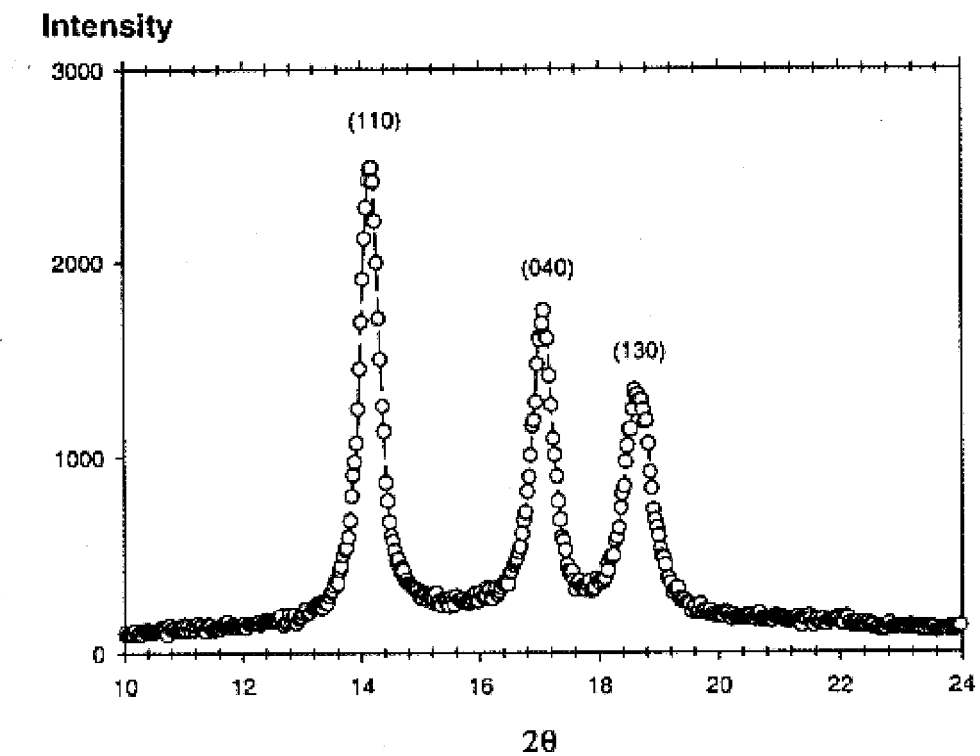
FIG. 15 is a 2-D scan of spunbond polypropylene fiber with scattering perpendicular to the fiber axis. The Y axis shows intensity and the X axis represents 2θ.
Figure 16:
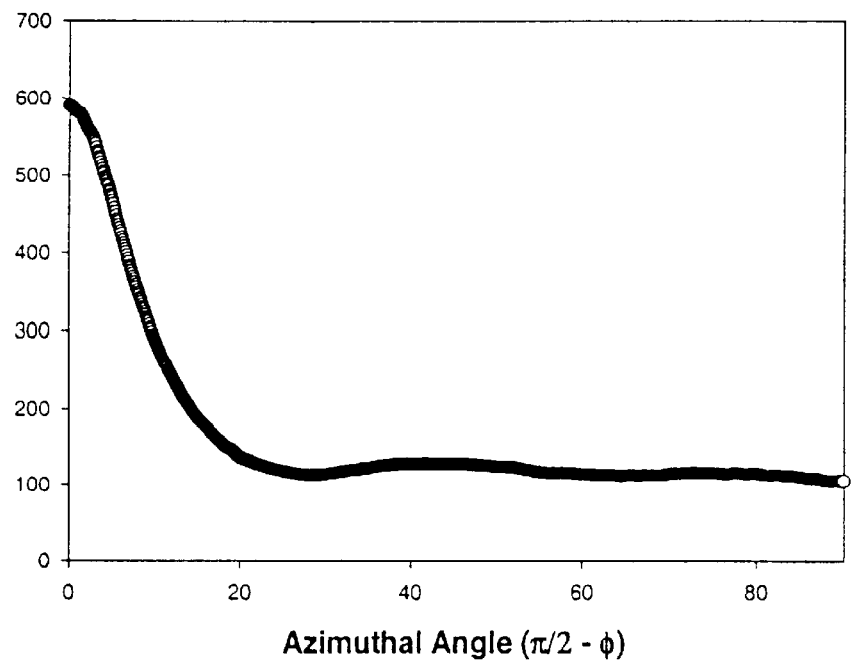
FIG. 16 is an azimuthal X-ray Intensity Distribution for specimen Control, (040) planes, transmission geometry.
Figure 17:
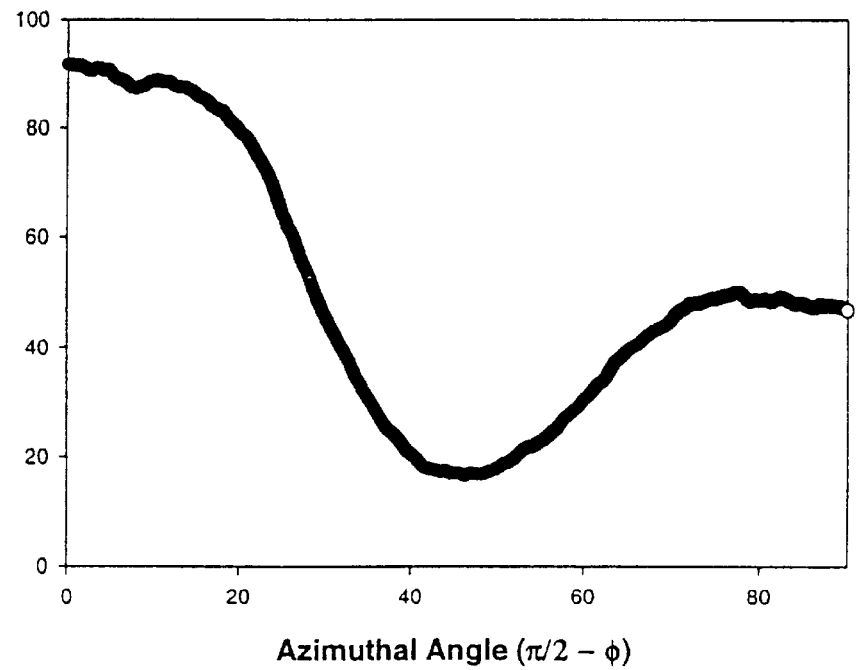
FIG. 17 is an azimuthal X-ray Intensity Distribution for specimen Cover 0, (040) planes, transmission geometry.
Figure 18:
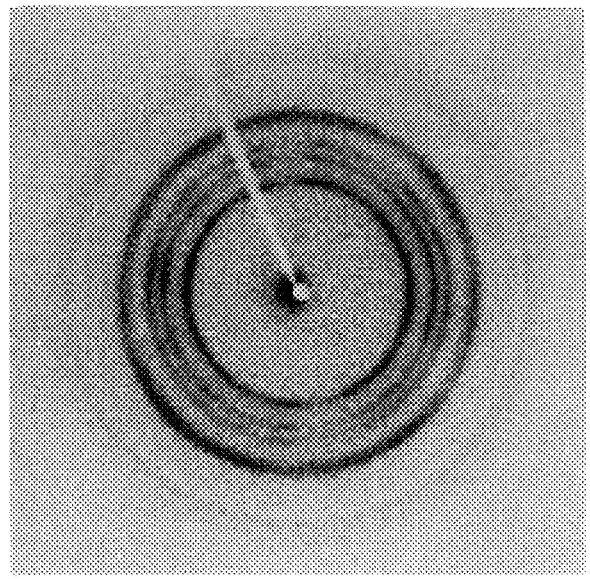
FIG. 18 is a 2-D X-ray intensity distribution, transmission geometry, for specimen: Cover 2, MD vertical, X-ray perpendicular to the plane of paper.
Figure 19:
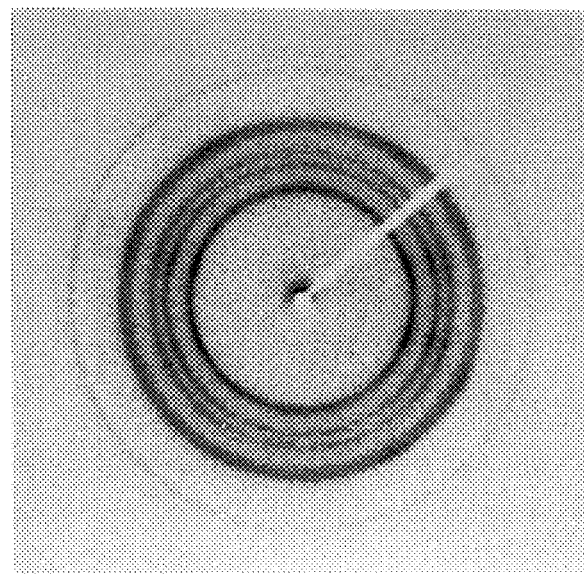
FIG. 19 is a 2-D X-ray intensity distribution, transmission geometry for specimen: Cover 6, MD vertical, X-ray perpendicular to the plane of paper.
Figure 20:
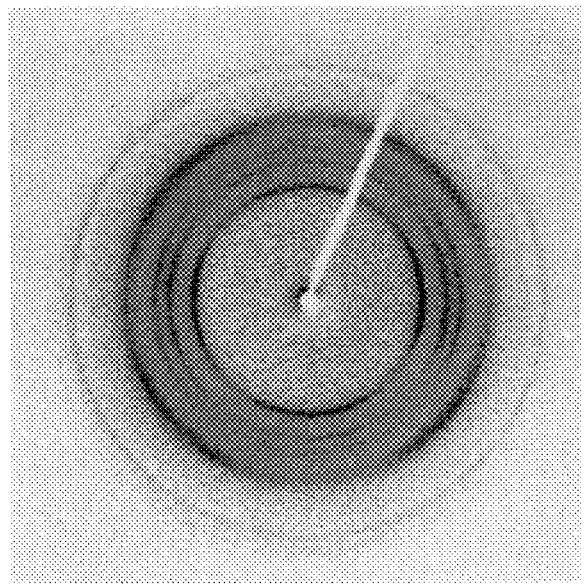
FIG. 20 is a 2-D X-ray intensity distribution, transmission geometry for specimen: Cover 7, MD vertical, X-ray perpendicular to the plane of paper.

In FIGS. 13 and 14 are shown the 2-D intensity patterns of the fiber specimen (Control) and the SB fabric (Cover 0), respectively in transmission geometry. The crystallographic indexes of the planes giving rise to the respective X-ray intensity maxima are labeled in FIG. 15. The amorphous background was subtracted from the 1-D intensity distributions in radial directions, which correspond to a 2$\theta$ scans at fixed azimuthal angles. An example of such intensity curve is shown in FIG. 15 (specimen Cover 0, equatorial scan). In FIG. 16 and 17 are given the azimuthal intensity distributions from planes (040) for the two specimens. It is apparent that the crystalline ODF is much sharper than the fibers ODF in the plane of the fabric. The orientation factors for the two specimens were computed from equations (4)–(6) and the results are $f_H=0.8$ and $f_f=0.34$. If we correct the SB fabric scattering curves for the crystal axis distribution via equation (17), the result is $f_f=0.37$. Thus the error in the computation of $f_f(\phi)$, resulting from nonperfect crystalline alignment is less than 10%. In view of the relatively small error this correction was not applied in the computation of the orientation factors of specimens Cover 2, Cover 6 and Cover 7. The 2-D intensity transmission patterns for these specimens are shown in FIGS. 18, 19 and 20, respectively. The orientation factors in the plane ($f_f(\phi)$) of the SB fabrics are summarized in Table A.

TABLE A

| Specimen | $f_f(\phi)$ |
|---|---|
| Control | 0.81 |
| Cover 0 | 0.34 |
| Cover 2 | 0.21 |
| Cover 6 | 0.05 |
| Cover 7 | 0.18 |

The in-plane fibers orientation factor of the creped fabrics (Cover 2–Cover 7) is generally lower than the uncreped fabric (Cover 0). This denotes that creped spunbond has more fiber elements or components of fiber elements that are oriented in the X-direction compared to spunbond. Since the value of the in-plane fibers orientation factor is approaching zero for some creped spunbonds (Cover 6), this is an indication that creping additionally randomizes the fibers. For fiber elements that were truly random in the plane of the fabric $f_f(\phi)=0$.

Fiber Axis Distribution Perpendicular to the Plane of the Fabric (YOZ in FIG. 5)

Figure 21:
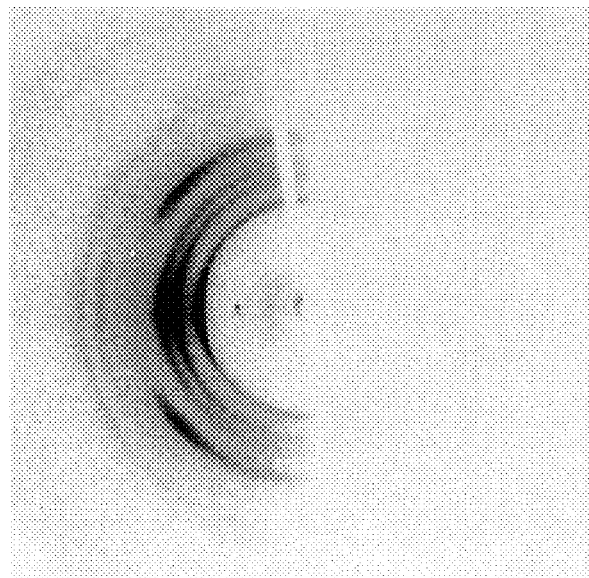
FIG. 21 is a 2-D X-ray intensity distribution, reflection geometry for specimen: Cover 0, MD vertical.
Figure 22:
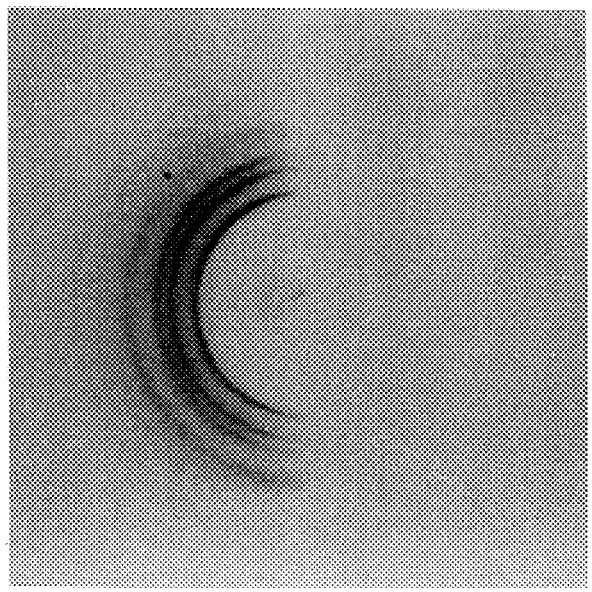
FIG. 22 is a 2-D X-ray intensity distribution, reflection geometry for specimen: Cover 2, MD vertical.
Figure 23:
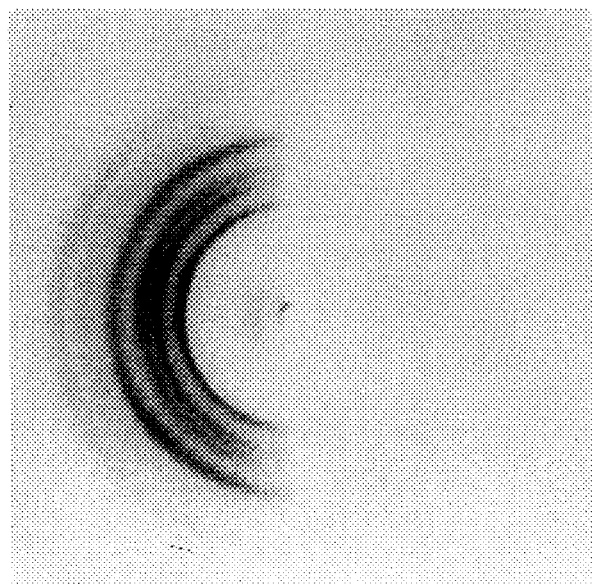
FIG. 23 is a 2-D X-ray intensity distribution, reflection geometry for specimen: Cover 6, MD vertical.
Figure 24:
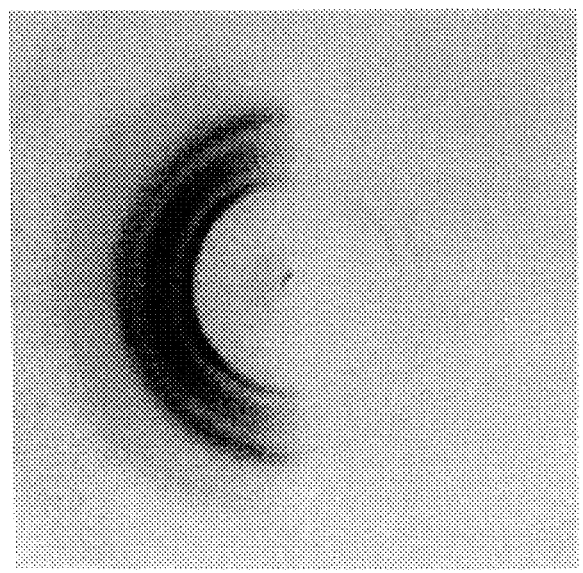
FIG. 24 is a 2-D X-ray intensity distribution, reflection geometry for specimen: Cover 7, MD vertical.

In FIG. 21 is shown the 2-D pattern of specimen Cover 0 in reflection geometry. The sharpness of the intensity maxima reflects the fact that the fiber axes lie in the plane of the fabric. A comparison with FIG. 22, which shows the 2-D pattern of specimen Cover 2, indicates that after the fabric was creped a substantial portion of fiber segments exhibit perpendicular orientation. The same is true for specimens Cover 6 and Cover 7 (FIGS. 23 and 24 respectively). The azimuthal curves were corrected for amorphous background and absorption. The computational procedures are similar to the previous case and the orientation factors are summarized in Table B.

TABLE B

| Specimen | $f_f(\psi)$ |
|---|---|
| Cover 0 | 0.87 |
| Cover 2 | 0.25 |
| Cover 6 | 0.36 |
| Cover 7 | 0.39 |

The fiber orientation factor for specimen Cover 1 was obtained after correction of the experimental curve for crystal orientation distribution. In view of the low orientation factors (Table B) this correction was not applied for the rest of the specimens. The rapid decrease of the perpendicular f-ODF is a manifestation of the 3-D randomization upon creping. The out-of-plane fibers orientation factor ($f_f(\psi)$) of the creped fabrics (Cover 2–Cover 7) is generally lower than the uncreped fabric (Cover 0). This denotes that creped spunbond has more fiber elements or components of fiber elements that are oriented in the Y-direction compared to spunbond. For the covers studied, creping spunbond causes some fiber elements to be oriented out of the plane of the fabric.

Since randomization as a rule leads to increase of the specimen volume, while the volume of the fibers (i. e. the occupied volume) remains constant, it should lead to increase of the average pore size.

As shown above, the average fiber orientation along any specified direction of a SB fabric can be derived from the two dimensional X-ray intensity distribution in at least two mutually perpendicular planes. The method herein is consistent and theoretically sound. It is particularly well suited for X-ray studies utilizing 2-D X-ray detector.

TransEpidermal Water Loss (TEWL) (Test Method I)

Skin hydration values are determined by measuring TransEpidermal Water Loss (TEWL) and can be determined by employing the following test procedure.

The test is conducted on adults on the forearm. Any medications should be reviewed to ensure they have no effect on test results and the subject's forearms should be free of any skin conditions such as rashes or abrasions. Subjects should relax in the test environment, which should be at about 72° F. (22° C.) with a humidity of about 40 percent, for about 15 minutes prior to testing and movement should be kept to a minimum during testing. Subjects should wear short sleeve shirts, not bathe or shower for about 2 hours before testing, and should not apply any perfumes, lotions, powders, etc, to the forearm.

The measurements are taken with an evaporimeter, such as an Evaporimeter EP1 instrument distributed by Servomed A B, Stockholm, Sweden.

A baseline reading should be taken on the subject's forearm and should be less than 10 $g/m^2/hr$. Each test measurement is taken over a period of two minutes with TEWL values taken once per second (a total of 120 TEWL values). The digital output from the Evaporimeter EP1 instrument gives the rate of evaporative water loss (TEWL) in $g/m^2/hr$.

For testing, the end of a dispensing tube is placed on the mid-forearm. An armband is placed on the subject's forearm directly over the end of the tube. The eye of the tube should be facing the target loading zone.

Hold the product in place with tape without allowing it to come in contact with the subject's skin. For the testing herein, the product was a HUGGIES ULTRATRIM Step 3 diaper having 8.9 gms of superabsorbent placed in a zone about 2.5 inches (63.6 mm) wide and the standard liner was replaced with the web to be tested.

Place a stretchable net such as that available from Zens Industrial Knit Products of Milwaukee, Wis., over the product to help to hold it in place.

Three equal loadings of 60 ml of physiologic saline available from VWR Scientific Products (800-932-5000) at about 95° F. (35° C.) are delivered to the product at an interval of 45 seconds by a pump such as a MASTERFLEX Digi-Static batch/dispense pump. After 60 minutes, the product is removed from the subject's forearm and Evaporimeter readings taken immediately on the skin where the product had been.

TransEpidermal Water Loss values are reported as the difference between the one hour and baseline values in $g/m^2/hr$.

Artificial Menses Preparation (Test Method J)

The artificial menses fluid used in the testing was made from blood and egg white by separating the blood into plasma and red cells and separating the white into thick and thin portions, where "thick" means it has a viscosity after homogenization above about 20 centipoise at 150 $sec^{-1}$, combining the thick egg white with the plasma and thoroughly mixing, and finally adding the red cells and again thoroughly mixing. Blood, in this example defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition or anti-coagulant chemicals and others. The blood must be non-coagulating in order to be useful and any method which accomplishes this without damaging the plasma and red cells is acceptable.

Jumbo chicken eggs were separated, the yolk and chalazae discarded and the egg white retained. The egg white was separated into thick and thin portions by straining the white through a 1000 micron nylon mesh for about 3 minutes, and the thinner portion discarded. The thick portion of egg white which was retained on the mesh was collected and drawn into a 60 cc syringe which was then placed on a programmable syringe pump and homogenized by expelling and refilling the contents five times. The amount of homogenization was controlled by the syringe pump rate of about 100 ml/min, and the tubing inside diameter of about 0.12 inches. After homogenizing the thick egg white had a viscosity of about 20 centipoise at 150 $sec^{-1}$ and was then placed in the centrifuge and spun to remove debris and air bubbles at about 3000 rpm for about 10 minutes After centrifuging, the thick, homogenized egg white, which contains ovamucin, was added to a 300 cc FENWAL® Transfer pack container using a syringe. Then 60 cc of the swine plasma was added to the FENWAL® Transfer pack container. The FENWAL® Transfer pack container was clamped, all air bubbles removed, and placed in a Stomacher lab blender where it was blended at normal (or medium) speed for about 2 minutes. The FENWAL® transfer pack container was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336–1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1 194Z03127: Separation Technology, Inc., 1096 Rainer Drive, Altamont Springs, Fla. 32714.

Contact Angle Measurements (Test Method K)

Static contact angle measurements were conducted using artificial menses on film surfaces. These surfaces were either treated or unmodified as described in this work. Drops which measured 0.5 to 2 mm in height were applied to the surface of the film with a tapered tip using a syringe and a programmable pump (Harvard Apparatus PHD 2000). A Leica Wild M3Z stereoscopic microscope was tilted on edge to view the drop of fluid as it was applied to the film surface. A Sony DKC-5000 digital photocamera 3CCD recorded the application of the fluid to the surface. Later, contact angle measurements were made on the individual drops of fluid as they contacted the surface using an image analysis program. Five measurements of contact angle were made on each side of the drop and averaged. A total of five to ten drops were measured for each film and averaged.

DETAILED DESCRIPTION OF THE INVENTION

The object of this invention is a unique material whose structure and surface energy may be tailored for use in absorbent articles. More preferably this invention refers to the selective design of a material for use as a cover or liner for absorbent articles wherein the article delivers improved fluid functionality and the aesthetics and comfort associated with fibrous materials.

Figure 3:
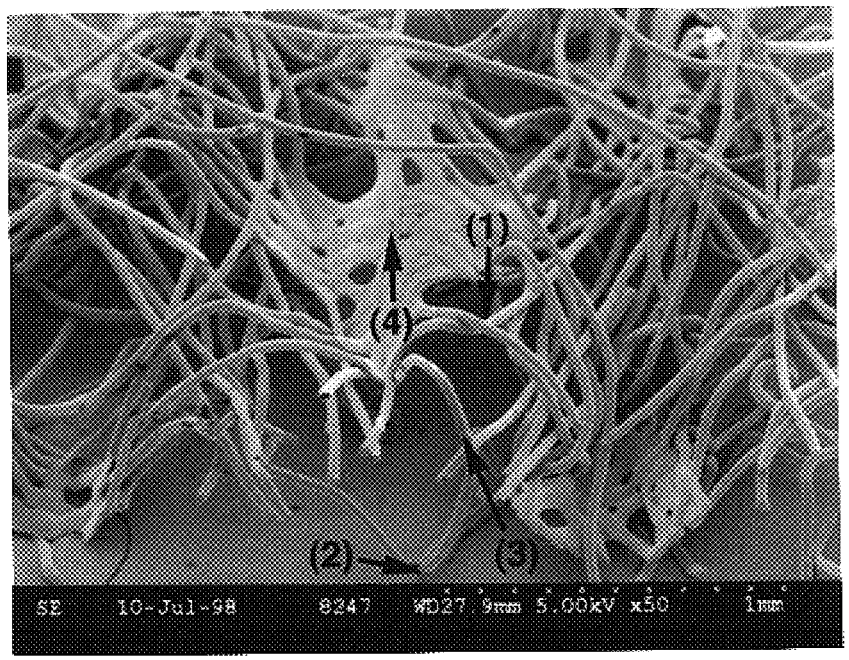
FIG. 3 is an Scanning Electron Microscope (SEM) micrograph of a material according to the invention.
Figure 4:
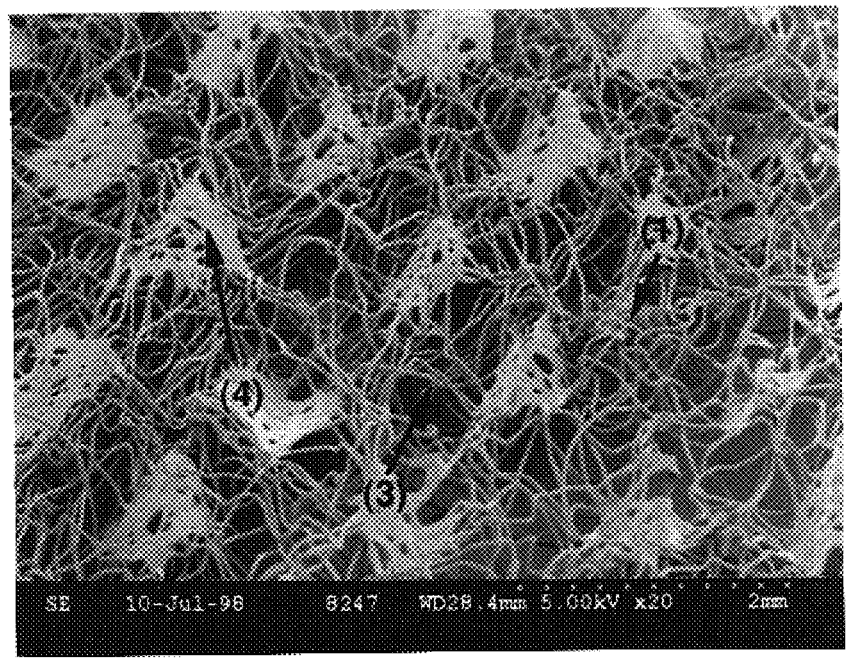
FIG. 4 is an SEM micrograph of a material according to the invention.

The object of the invention is provided, as illustrated in FIGS. 3 and 4, by a material which can be defined by two surfaces, an upper region which is commonly referred to as the top surface (1) and a lower region which is referred to as the lower surface (2) (not visible in FIG. 4). Substantially fiber-like elements (3) define each of these surfaces and extend from one surface to the other, presumably intersecting one or both of these planes. Deformed, discontinuous, film-like regions (4) connect individual fibers and act as regions of stability. These are denoted as areas of increased stress concentration when subjected to an applied load. These regions of stability are noted by intersection, continuity, or merging of one or more of the fiber-like elements. These regions may be created through one or both of the following typical methods: physical or chemical bonding, which may be produced through traditional means such as thermal bonding or adhesive bonding. Deformation such as described in this invention could be the result of physical or chemical forces. An example of the former could include but is not limited to mechanical stretching or draw.

The material of this invention is distinctly unique based on three key characteristics: 1) fiber-like element orientation, 2) the relationship of fiber-like elements relative to one another in 3-dimensional space, and 3) the caliper of the material. These elements are most suitably described using the following parameters over the ranges described herein as 1) $f_f(\psi)<0.87$, 2) $SA/VV<186$ cm$^2$/cm$^3$, and 3) caliper<0.150 inches. A representative material defined by this invention is creped spunbond and a detailed explanation of this material is provided in example 1.

The dimensionality of a material can be characterized by three coordinate axes X, Y, and Z which are mutually orthogonal and normal with respect to one another. A one dimensional feature may be described as a line, a 2 dimensional feature as a plane, and a three dimensional feature as an object. The materials described herein are 3 dimensional and may be better represented by the illustration in FIG. 5. As noted, three coordinate axis are discussed X, Y, and Z which are mutually orthogonal and normal with respect to one another. The Z axis is arbitrarily chosen to represent the machine direction of the material whereas the X direction represents the cross-direction of the material. The X and Z coordinate axes, therefore, define the plane of the material. The Y coordinate axis defines the bulk or thickness of the material. The X and Y axes and the Z and Y axes define the out of the plane coordinate system.

Figure 6:
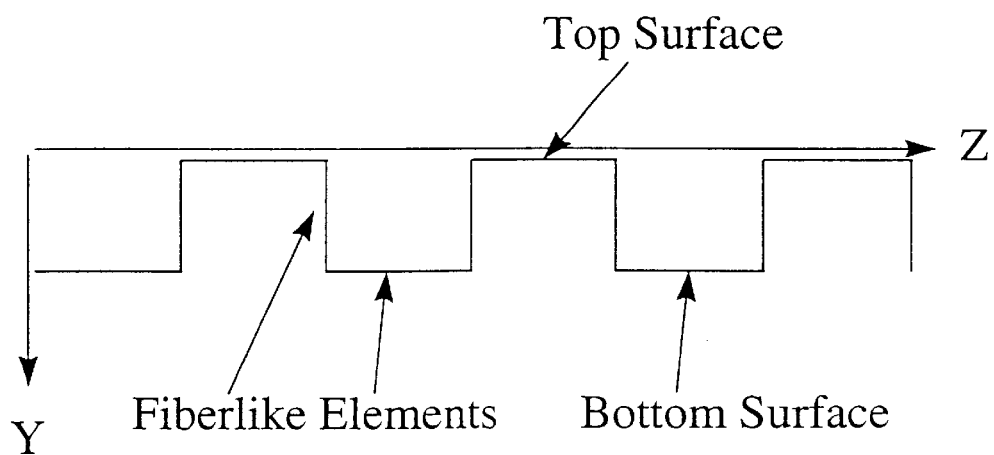
FIG. 6 is a representation of a web having flat surfaces.
Figure 7:
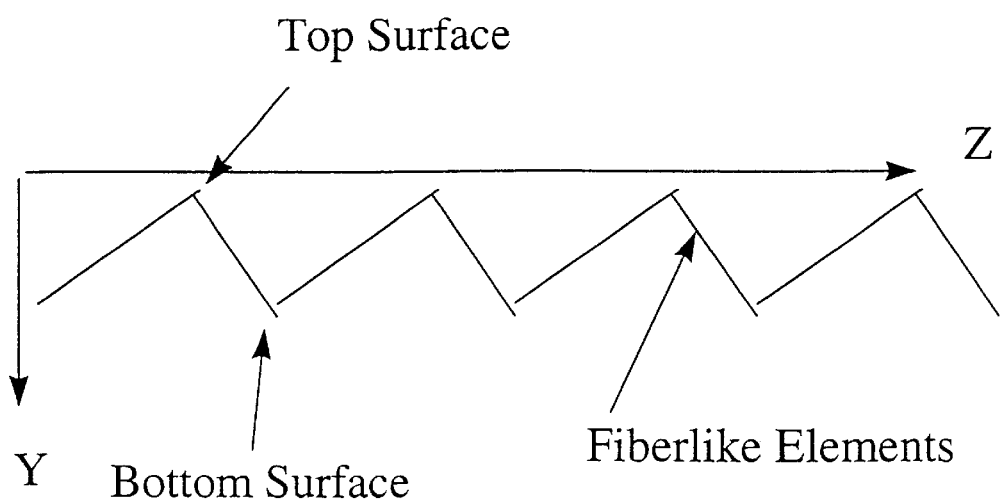
FIG. 7 is a representation of a web having undulating surfaces.

The fiber-like elements are arranged in three dimensional space and define a structure consisting of an upper and lower surface and preferably interconnected pathways therebetween. The configuration of these elements as viewed out of the plane is important for the movement of fluid. The elements may be flat as shown in FIG. 6 or undulating as shown in FIG. 7. It is believed that the organization of these elements could be optimized for the intended application. For instance, materials with undulating surfaces may provide more ideal fluid handling for fluids with viscous or viscoelastic character, fluids at low volumes and insulted such that they have low momentum or with low external pressure applied to the material in an absorbent article. Conversely, materials with flat surfaces may provide better fluid handling for elastic fluids, fluids at larger volumes and insulted such that they have reasonable momentum or high external pressure applied to the material in an absorbent article.

Figure 8:
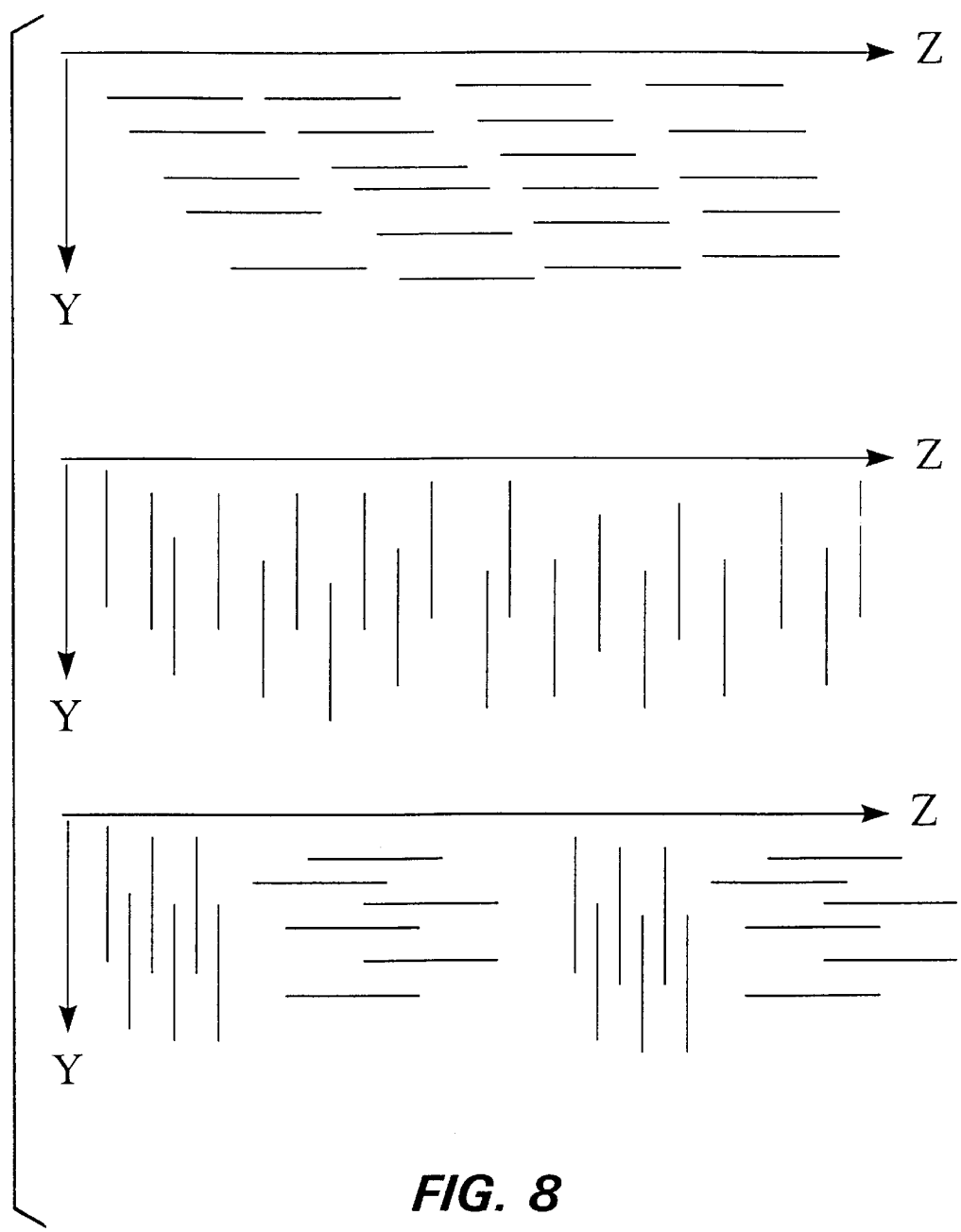
FIG. 8 has three views, a, b, and c.

The degree of orientation of the elements describes an important premise of the invention and can be described in two dimensions using Hermann's orientation factor which is represented by the following equation:

$$i\ f_f = (3<\cos^2\psi>-1)/2 \qquad \text{Equation(18)}$$

where $f_f$ is the orientation and $\psi$ is the angle between two arbitrary coordinate axes. The orientation may be denoted as "$f_f$" with a subscript defining the two axes, e.g. $f_{fzy}$, or as an "$f_f$" with a subscript defining the angle between the two axes, e.g. $f_f(\psi)$, where the angle between the Z and Y axes is the angle $\psi$. The application of this function is described in three model situations in FIG. 8 utilizing the Z and Y axes as a reference. FIG. 8a shows a case where $\psi=0$, cos $(\psi)=1$, and $f_f(\psi)=1$ where all the elements are oriented in the direction of the Z-axis. FIG. 8b shows a case where $\psi=/2$, cos $(\psi)=0$, and $f_f(\psi)=-1/2$ where all the elements are oriented in the direction of the Y-axis. FIG. 8c represents the isotropic case where $\psi\sim=54.7$ degrees, cos $(\psi)=0.578$, and $f_f(\psi)=0$ In this case an equal number of elements or components of elements are oriented in the directions of Y and Z.

Another important characteristic of the material is the configuration or distribution of fiberlike surfaces in three dimensions. Since fluid moves along the fiber surfaces but travels in the void volume of the material, one means for this characterization is the use of Surface Area(SA)/Void Volume (VV). This definition is defined incorporating denier since this is an eloquent way to account for essentially round or shaped fiber-like elements. A derivation of the parameters for this evaluation are given below:

$$i\ dpf = \pi * r^2 * 9 \times 10^5 * \rho f \qquad \text{Equation(19)}$$

$$i\ r = [dpf/(\pi * 9 \times 10^5 * \rho f)]^{1/2} \qquad \text{Equation(20)}$$

where; r=fiber radius in cm, $\rho_f$=density of fiber, I=length of the fiber, $\rho_{web}$=web density, dpf=denier per fiber and $\pi=3.14159$.

$$i\ SA/mass = (2*\pi*r*I)/(\pi*r^2*I*\rho_f) = 2/(r*\rho f) \qquad \text{Equation(21)}$$

$$i\ VV/mass = (1/\rho_{web}) - (1/\rho_f) \qquad \text{Equation(22)}$$

$$SA/VV = 2/([dpf/(\pi*9\times10^5*\rho_f)]^{1/2} * [(\rho_f/\rho_{web})-1]) \qquad \text{Equation(23)}$$

From equation 23, one observes that SA/VV is a function of fiber denier, web density and fiber density.

The material caliper is also essential to the definition of this material since it defines the distance that is necessary for a fluid to travel before it encounters other components of the absorbent article. For the purpose of this invention, this distance has been to be essentially equivalent to or less than 0.150 inches.

The fiberlike elements of this invention may be produced from but are not limited to polymers, polyolefins, plastomers, elastomers, foams, natural fibers, synthetic fibers, or blends/combinations of these components. The elements typically have a denier between 1 to 10 dpf and a basis weight between about 0.1 and 4.0 osy (3.4 and 136 gsm).

The use of $f_r(\psi)$, SA/VV, and caliper has suitably defined the material of this invention by the distribution, orientation and organization of fiber-like elements in three dimensions. Two extensive properties which are directly related to the intensive properties described above are the permeability and pore size. These parameters further define the material of this invention. The out-of-plane permeability and pore size are defined by the test method described in this application. A preferable material would have an out-of-plane permeability greater than 1000 darcies and more preferably greater than 2000 darcies. A preferable material would have less than 80% pores(based on cc/g) with radius less than 100 microns or more preferably less than 40% pores(based on cc/g) with radius less than 100 microns. In the most preferred case, the preferable material would have less than 20% pores(based on cc/g) with radius) with radius less than 100 microns.

Another important feature of this invention is the surface energy. The surface energy is characteristically defined by the contact angle a fluid makes with the surface of the material. A contact angle greater than 90 degrees represents a hydrophobic material whereas one with contact angle less than 90 degrees represents a hydrophilic material. A preferred material should consist of at least some fiber-like elements or regions of fiber-like elements, i.e., having a wettable character or a contact angle less than 90 degrees.

The structure can be rendered wettable through conventional means such as the application of a surfactant. Commercial surfactants such as Ahcovel Base N-62 (ICI Surfactants, Wilmington, Del.), Atmer 8174 (ICI), Masil SF-19 (PPG Industries, Gurnee, Ill.), and Mapeg ML 400 (PPG).have been found to be acceptable. Whichever surfactant is applied, the contact angle of menstrual simulant on the surface should be lower than that of an untreated structure. The surface should preferably have a contact angle measured with menstrual simulant less than 90 degrees.

Additionally, the material can be rendered wettable through application of surfactants either topically or internally, surface modification or treatment, surface chemistry, polymer chemistry, fiber-like-element chemistry, surface grafting, or methods commonly known in the art to change modification of surface chemistry to render a material wettable. In this case, materials which are wettable are distinguished from those that are nonwettable in that the contact angle is less than that of an unmodified surface, and that they have a contact angle of less than ninety degrees.

In another embodiment, the surface characteristics are modified to provide properties beyond that anticipated with traditional treatments which render the structure wettable. One such treatment reduces promotes rapid intake and reduces protein deposition. The surface of such materials may be modified to alter the fluid, thereby altering its properties. One such treatment which has demonstrated these properties, is polyolefin oxide. Regions of the surface may be treated with, for example, polyethylene oxide and/or polypropylene oxide or block copolymers of these oxides. Typical commercial chemistries are block copolymers of ethylene oxide and propylene oxide sold under the tradename Pluronics® (BASF, Germany) and SYNPERONIC® (ICI Surfactants, Wilmington, Del.).

In yet another embodiment, the surface is modified with treatments which transfer to the skin and promote wellness. These treatments can include substances which may be used in conjunction with surfactants. Such treatments may include those known in the art to promote improvements in skin condition such as aloe, vaseline, dimethicone, vitamin k, etc.

In yet another embodiment, the surface energy of the upper material surface is lower than the surface energy of the lower surface creating a surface energy gradient between surfaces. Such a gradient can promote fluid movement from the upper surface to the lower surface. Pore size gradients may also be generated such that the average pore size of a first volume of material incorporating the upper surface is different than the average pore size of a second volume of material incorporating the lower surface wherein the first and second volumes are exclusive of one another. The nature and type of the fluid will dictate whether it is preferential to have the average pore size of the first volume to be larger or smaller than the average pore size of the second volume. For the case of viscoelastic fluids, it may be preferable to have the average pore size of the second volume to be larger than that of the first volume. Materials may also be created with pore size and wettability gradients.

The materials mentioned above may be specifically tailored for use in applications for personal use or care. The material may be used as a topsheet in products for infant care, feminine care, adult care, health care. These can include applications for managing newtonian fluids such as urine, viscoelastic fluids such as menstrual fluid and feces (BM), or viscous fluids such as blood.

In one preferred embodiment, the material of this invention is especially useful for feminine care absorbent articles to manage menstrual fluid or discharge. Typical feminine care products such as pads, pantiliners, and tampons.are made from multiple materials and generally consist of a cover, also known as topsheet or body side liner. Beneath the cover, one or more absorbent layers are usually present for functions such as intake, distribution, retention, or body shaping. Beneath the absorbent is usually a fluid impermeable layer called a baffle, which may be made of film.

Proper fluid management for a topsheet in feminine care absorbent articles requires good intake (absorbency), low staining (clean), low rewet (dry) and low fluid retention (dry). The material must also deliver these attributes under a wide range of pressure and flow conditions. A product may, for instance, experience variable flow consisting of both low continuous flow or sudden heavy flow. The product may also experience conditions of no pressure, low or light pressure, or high pressure. Additionally, the cover must also be capable of managing menstrual discharge which can exhibit a broad range of viscosity and elasticity.

The material of this invention is preferred for use as a cover, which, in conjunction with an absorbent core, permits superior management of viscous or viscoelastic fluids such as menstrual discharge for personal care articles, while delivering acceptable aesthetic properties such as softness. Compared to nonwovens such as spunbond, the material of this invention is particularly suitable for the fluid management expected of high performance liners or topsheets in feminine care absorbent articles or to replace costly liner/surge materials. The low SA/VV, out-of plane fiber orientation, and material caliper in conjunction with appropriate surface wettability help to overcome many of the limitations associated with nonwovens. For instance, out-of-plane fiber orientation can improve wicking to absorbent layers and also may increase permeability providing better intake. Materials with low SA/VV are typical of highly permeable structures with large average pore size. Such materials generally promote excellent absorbency, low staining, and low fluid retention. By providing the other material characteristics in conjunction with some critical thickness, rewet may be reduced by proving a barrier to flowback. Additionally, the use of the material of this invention in an absorbent article for feminine care offers the aesthetics and comfort properties which are inherent to nonwovens and thus far unattainable with apertured film covers.

By tailoring the SA/VV, out-of-plane fiber orientation, caliper, and wettability in this material within the ranges specified in the materials invention, functional properties of a liner/absorbent system such as those in feminine care articles may be optimized. The examples of this application denote some means by which these material characteristics are tailored to provide optimal fluid functionality.

However, one must note that the exudates typical of menstrual discharge are highly variable through the menstrual cycle and from each female. A fully optimized cover material would be designed around the average and extreme properties typical of these fluids. Thus, optimal material properties must be gauged based on the use of menstrual simulants which represent or mimic typical menstrual properties.

In one preferred embodiment, the material is used in infant care products as a liner or topsheet for diapers. A typical diaper is made from multiple materials and generally consists of a topsheet or liner next to the wearer. Beneath the cover, one or more absorbent layers are usually present for functions such as intake, distribution, retention. Beneath the absorbent is usually a fluid impermeable layer called a baffle or outercover, which may be made of film.

Proper functioning as a diaper liner requires good intake properties such that the incoming liquid is transported completely through it and hence, minimal pooling and spreading of the liquid at the top surface occurs. Pooling and spreading by the liquid at the surface can contribute to leakage and skin hydration. Additionally, the body-contacting surface of the liner should have minimal saturation so that skin hydration does not increase. It is desirable that personal care articles be designed so as to minimize skin hydration since it contributes to the occurrence of diaper rash.

High conductance (permeability divided by thickness) is required for complete transmission of liquid through the liner/cover material. It has been found that for typical liquid insult rates of 20 cc/second, a liner conductance of greater than 100 darcies/mil is required for all of the liquid to pass through. This means that for a liner with a thickness of 10 mils, its permeability should be greater than 1000 darcies. It has also been established that lower skin hydration levels as measured by TEWL are achieved with liners that have a conductance greater than 100 darcies/mil.

An additional example of the use of the material of this invention is in a diaper in conjunction with various outer-covers and other materials. The outercover is sometimes referred to as the backsheet cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Backings may also serve the function of a mating member for mechanical fasteners, in the case, for example, where a nonwoven fabric is the outer surface. The material of this invention has been found to function well in a dual layered embodiment where the other layer is hydrophobic. Such a dual layer structure may be used as a liner in a diaper with the hydrophobic layer toward or away from the wearer, though the orientation toward the wearer is preferred.

The material of this invention may also be utilized in health care products such as surgical drapes and gowns, fenistration materials, and wound care dressings and application.

In wound care dressing applications, the material of this invention can be used to provide an absorbent but dry top surface which provides comfort and softness. It can also provide an absorbent but dry top surface which reduces sticking to the wound when removed. Careful selection of the composition of fiber-like elements may also help to reduce sticking.

TABLE 1

| Cover | Target Denier (dpf) | Pre-creping B.W. (osy) | Crepe Level (%) | Treatment | Actual Creped B.W. (osy) | Caliper Actual (in) | Density Actual (g/cc) | Fiber Radius (microns) | SA/mass $cm^2/g$ | VV/mass $cm^3/g$ | SA/VV $cm^2/cm^3$ | Permeability | Pore Radius* microns |
|---|---|---|---|---|---|---|---|---|---|---|---|---|---|
| 0 | 3.5 | 0.4 | N, 0% | A | NA | 0.006 | .089 | 11.66 | 1884 | 10.14 | 185.9 | NM | NM |
| 1 | 3.2 | 0.6 | N, 0% | A | NA | 0.008 | 0.100 | 11.15 | 1970 | 8.89 | 221.7 | 511 | 116 |
| 2 | 3.5 | 0.4 | Y, 30% | A | 0.64 | 0.026 | 0.033 | 11.67 | 1884 | 29.33 | 64.24 | 3953 | 310 |
| 3 | 2.1 | 0.4 | Y, 30% | None | 0.63 | 0.026 | 0.032 | 9.04 | 2432 | 29.81 | 81.60 | 2389 | 248 |
| 4 | 3.5 | 0.4 | Y, 30% | None | 0.64 | 0.026 | 0.033 | 11.67 | 1884 | 29.33 | 64.24 | 3953 | 310 |
| 5 | 5 | 0.4 | Y, 30% | None | 0.71 | 0.031 | 0.031 | 13.94 | 1576 | 31.61 | 49.88 | 7593 | 395 |
| 6 | 2.1 | 0.4 | Y, 30% | A | 0.63 | 0.026 | 0.032 | 9.04 | 2432 | 29.81 | 81.60 | 2389 | 248 |
| 7 | 5 | 0.4 | Y, 30% | A | 0.71 | 0.031 | 0.031 | 13.94 | 1576 | 31.61 | 49.88 | 7593 | 395 |

TABLE 1-continued

| Cover | Target Denier (dpf) | Pre-creping B.W. (osy) | Crepe Level (%) | Treatment | Actual Creped B.W. (osy) | Caliper Actual (in) | Density Actual (g/cc) | Fiber Radius (microns) | SA/mass cm^2/g | VV/mass cm^3/g | SA/VV cm^2/cm^3 | Permeability | Pore Radius* microns |
|---|---|---|---|---|---|---|---|---|---|---|---|---|---|
| 8 | 2.1 | 0.2 | Y, 30% | A | 0.46 | 0.02 | 0.031 | 9.04 | 2432 | 31.47 | 77.31 | 3367 | 256 |
| 9 | 2.1 | 0.6 | Y, 30% | A | 0.83 | 0.032 | 0.034 | 9.04 | 2432 | 28.68 | 84.81 | 1535 | 226 |
| 10 | 3.5 | 0.6 | Y, 30% | A | 0.89 | 0.033 | 0.036 | 11.67 | 1884 | 26.67 | 70.64 | 3125 | 283 |
| 11 | 5 | 0.6 | Y, 30% | A | 0.88 | 0.037 | 0.032 | 13.94 | 1576 | 30.39 | 51.87 | 4669 | 383 |
| 12 | 3.5 | 0.4 | Y, 30% | B | 0.64 | 0.026 | 0.033 | 11.67 | 1884 | 29.33 | 64.25 | 3953 | 310 |

*calculated using the equation reff = 2 (VV/Sa) ref is Dunstan and Whi
Treatment "A" refers to 0.3 weight percent of AHCOVEL ® Base N-62 (ICI Surfactants, Wilmington, Delaware) added to the web.
Treatment "B" refers to 2.0 weight percent SYNPERONIC ® (ICI Surfactants, Wilmington, Delaware) added to the web.
NA refers to not applicable
NM refers to not measured

EXAMPLE 1

One representative material of this invention is spunbond fabric which has been creped in a manner similar to that of tissue. For the purpose of these examples this material will be known as creped spunbond. Creped spunbond was prepared using the following process method although alternative methods are conceivable. As shown in FIG. 1, a nonwoven web such as a spunbond web, which may be pretreated with surfactant to render it wettable, is unwound. For the purpose of these examples, webs were untreated prior to creping. An adhesive is applied to the web by printing, spraying, or other application process preferentially depositing on the side which will contact the roll. (2.) In this way, latexes or melt adhesives may be used. The web passes over a creping roll (4.) where it sticks to the surface due to a thin layer of adhesive. The web is then creped using a doctor blade/knife (5) and taken up at a speed less than the inlet speed. Crepe level is defined as the percent difference in the inlet and outlet speed.

Eleven different creped spunbond samples were prepared for the purpose of this example and to demonstrate material characteristics and functional differences between creped spunbonds and spunbonds as well as to illustrate differences within the class of creped spunbond materials. These materials are summarized in Table 1. Note that the creped spunbond materials (covers 2–12) differ in target denier, creped basis weight, and treatment. All creped spunbonds for this example were prepared at a crepe level of 30% although other crepe levels are readily attainable. Additionally all the spunbond fabrics were produced using 92 weight % of E5D47 polypropylene (Union Carbide) and 8 weight % of Ampacet 41438 $TiO_2$ concentrate. The fiber density for all webs in the Examples was 0.91 g/cc. The creping adhesive was Hycar 26684 latex (B.F. Gooodrich) at a 36% solids emulsion applied at 0.5–1.0% wet add-on by rotogravure printing. Inlet line speed was 300 feet/minute on a 40-inch diameter creping roll at 160° F. (71° C.) with a doctor blade holder angle of 28°. The fabrics were post-treated with surfactant, as specified in the examples, with surfactant by either spray or dip/vacuum extraction methods.

As shown in Table 1, cover 2 is a 3.5 dpf, 0.4 osy spunbond web that has been creped to a level of 30% yielding a creped spunbond with actual creped basis weight of 0.64 osy, thickness of 0.026 inches, and density of 0.033 grams/cc. The web was post-treated to yield creped spunbond with 0.3 weight percent Ahcovel® Base N-62 (ICI Surfactants, Wilmington, Del.). Similarly, information for covers 3–12 can be obtained from Table 1. Covers 0 and 1 are spunbond fabrics which are uncreped and were added to this table for reference to demonstrate the effects of creping spunbond on both structural and functional properties.

Representative materials from Table 1 were chosen to illustrate the effects of creping on structural characteristics of spunbond. For this exercise, cover 0 and cover 1 will be representative spunbond webs and cover 2 will be a representative creped spunbond web. As noted from Table A and B, creped spunbond has more fiber elements or components of fiber elements oriented along the X direction compared to spunbond when observing the X-Z plane (in the plane) of the fabric. For the Y-Z plane (out of the plane) of the fabric, creped spunbond has more fiber elements or components of fiber elements oriented along the Y direction compared to spunbond. Therefore fiber-like elements are being oriented out-of-the plane of the fabric when spunbond is creped to produce creped spunbond. These trends are shown quantitatively by values of $f_i(\psi)$ for cover 0 of 0.34 and cover 2 of 0.21 and for values of $f_j(\psi)$ for cover 0 of 0.87 and cover 2 of 0.25.

As shown in Table 1, the creped spunbonds have much higher caliper than spunbond. For instance, cover 0 has a caliper of only 0.006 inches compared to that of 0.026 inches for cover 2.

The SA/VV is much lower for the creped spunbonds than the spunbonds as illustrated by a value of 185.89 for cover 0 compared to 64.24 for cover 2.

The pore size distribution and permeability is also vastly different for spunbond and creped spunbond, a result which is expected based on the change in intensive properties of material caliper, fiber orientation, and SA/VV. FIG. 2 depicts the pore size distribution for covers 1 and 2 using test method B. The graph in FIG. 2 depicts the volume of pores (cc/g of material) which have a particular pore radius. As exhibited by the area under the curves, one notes that Cover 2 has a larger void volume than Cover 1. Additionally, Cover 2 has a much larger peak pore size than Cover 1 with few pores less than 100 microns in radius. One also notes that the pore size distribution broadens when spunbond is creped as exhibited by the breadth of the curve.

The permeability of the webs was measured using test method C, and the resulting values are depicted in table 1. One notes that cover 1 has a permeability of only 511 Darcies compared to that of 3953 darcies for cover 2.

Within the family of creped spunbond webs, Table 1, one also notes that SA/VV and permeability are directly related to the initial target denier and basis weight of the precreped spunbond web. As fiber denier increases from 2.1 dpf to 5.0 dpf at constant precreped spunbond basis weight, SA/VV decreases and out-of-plane permeability increases.

Conversely, as precreped spunbond basis weight increases from 0.2 osy to 0.6 osy at constant fiber denier, SA/VV increases and out-of-plane permeability decreases. The average pore size typically increases with increasing fiber denier, but is only modestly affected by precreped basis weight.

EXAMPLE 2

Covers 1 and 2 were evaluated using test methods E, F and G. The results are given in Table 2.

TABLE 2

Functional properties for spunbond and creped spunbond

| Material | Average Intake Time (seconds) | Average Rewet (grams) | Average Stain Size (mm^2) | Average Fluid Retention (grams) |
|---|---|---|---|---|
| Cover 1 | 32 | 0.45 | 751 | 0.043 |
| Cover 2 | 17.49 | 0.07 | 619 | 0.015 |

It can be seen that Cover 2 had a faster intake time, lower rewet, smaller average stain size, and lower average fluid retention than did Cover 1. These considerable improvements were directly related to the material structure, including lower SA/VV, higher out-of-plane fiber orientation and higher caliper compared to spunbond. Creping the spunbond web cover, therefore, improved overall cover performance, moving closer to an ideal cover. Cover 2 also had lower stain intensity than Cover 1, presumably due to the high permeability which provided rapid intake, large average pore size which yielded low capillarity, and greater material caliper which provided fluid masking.

EXAMPLE 3

Untreated creped covers were compared to treated creped covers to understand the critical surface wettability required for intake. The surface energetics for these treatments were quantified using Test Method K and the intake properties were quantified using Test Method E. The untreated surface is a polyolefin surface which is known in the art to be relatively hydrophobic. The AHCOVEL® treatment on this surface renders it slightly wettable. For comparison, the contact angles were measured with menses simulant for 0.5% AHCOVEL® treatment on a model polyethylene surface (XP3134a, Edison Plastics, NewPort News, Va.) and were compared to an untreated polyethylene surface. The contact angle of the untreated surface was approximately 87 degrees while that of the treated surface was about 75 degrees.

As can be seen from the data in Table 3, the untreated Covers 3, 4 and 5, had exceedingly long intake times as compared with the treated Covers 2, 6 and 7. This suggests that the creped spunbond webs must be wettable to permit intake of fluid without applying external pressure. It is interesting to note that even applying surfactants such as Ahcovel® Base N-62 which have moderate to low wettability results in a substantial reduction in intake time.

TABLE 3

Impact of surface characteristics of creped spunbond structures

| Specimen | Intake Time (Seconds) |
|---|---|
| Cover 3 | >5 minutes |
| Cover 4 | >5 minutes |
| Cover 5 | >5 minutes |

TABLE 3-continued

Impact of surface characteristics of creped spunbond structures

| Specimen | Intake Time (Seconds) |
|---|---|
| Cover 6 | 18.78 |
| Cover 2 | 17.49 |
| Cover 7 | 13.23 |

EXAMPLE 4

Creped covers were produced from a matrix of spunbond webs which varied in basis weight and fiber denier to determine their impact on permeability. The effect of permeability is related to functional performance. Covers with varying fiber deniers and fabric basis weights were tested for permeability according to Test C. As shown in Table 4, the permeability increased with increase in fiber denier and decrease in basis weight.

TABLE 4

Effect of fiber denier and basis weight of spunbond web on creped spunbond permeability and thickness. Impact of structural characteristics on functional properties.

| Specimen | Permeability (Darcies) | Thickness (Inches) | Average Intake Time (seconds) | Average Rewet (grams) | Average Stain Size (mm$^2$) | Average Fluid Retention (grams) |
|---|---|---|---|---|---|---|
| Cover 8 | 3367 | 0.018 | 19.46 | 0.28 | 729 | 0.022 |
| Cover 6 | 2389 | 0.024 | 18.78 | 0.17 | 697 | 0.025 |
| Cover 9 | 1535 | 0.028 | 26.33 | 0.19 | 618 | 0.049 |
| Cover 2 | 3953 | 0.022 | 17.49 | 0.07 | 619 | 0.0145 |
| Cover 10 | 3125 | 0.037 | 19.11 | 0.09 | 756 | 0.022 |
| Cover 7 | 7593 | 0.027 | 13.23 | 0.07 | 572 | 0.011 |
| Cover 11 | 4669 | 0.034 | 13.86 | 0.09 | 672 | 0.016 |

In general, the intake time, average rewet, and average fluid retention decrease with increase in permeability or decrease in SA/VV for the creped spunbond covers.

EXAMPLE 5

Cover 2 and Cover 12 were compared according to Tests E and F to demonstrate the impact of treatment chemistry on fluid management properties. As seen in table 5, Cover 12 has much lower intake time than Cover 2 with only modest increases in rewet.

TABLE 5

Impact of treatment chemistry on functional performance

| Specimen | Intake Time (seconds) | Rewet (grams) |
|---|---|---|
| Cover 2 | 17.49 | 0.07 |
| Cover 12 | 6.37 | .102 |

EXAMPLE 6

Yet another cover, Cover 13, was developed to show the impact of both pore size gradients and surface treatment gradients on fluid management properties. Cover 13 was a creped spunbond web with a final basis weight of 0.4 osy. It was made from two layers which formed one material. The top layer was a 3.5 dpf section treated with 0.35 percent by volume and the bottom surface consisted of a 5.0 dpf section treated with 1.0 percent by volume SF-19. The 1.0 percent by volume SF-19 is known to be more wettable than the 0.3 percent by volume based on previous work. Covers 2 and 13 were evaluated using test methods E and F and the results are depicted in Table 6.

TABLE 6

| Specimen | Average Intake Time (seconds) | Average Rewet (grams) |
|---|---|---|
| Cover 2 | 17.49 | 0.07 |
| Cover 13 | 6.66 | 0.16 |

From this Table 6, one observes that pore size and wettability gradients can improve intake but typically increase rewet. An optimal gradient structure could be developed by tailoring the structure and surface chemistry of the creped material in one or more of the layers of the material.

EXAMPLE 7

Covers made according to this invention were tested for skin hydration according to the TEWL test as indicated above, specifically for applicability in diapers or where urine is the fluid of concern. Cover 14 was a 0.45 osy (15.26 gsm) two layer spunbond web made from Exxon 3315 polypropylene. The top layer was 0.15 osy (5 gsm), 2.5 denier fibers and the bottom layer was 0.3 osy (10.2 gsm), 4 denier fibers. The bottom layer also had about 1.25 weight percent of PPG's Masil SF-19 surfactant added. Cover 14 was creped to 20% according to the process described above. The creping adhesive was HYCAR 26684 applied at about 0.3 weight percent add-on to the web. Cover 14 had a permeability of 4335 darcies, a caliper of 0.023 inches and a conductance of 188 darcies/mil. Cover 15 was a 0.4 osy (13.6 gsm), 3.2 denier, single layer spunbond made from Union Carbide E5D47 polypropylene that was topically treated with about a 0.3 weight percent of AHCOVEL surfactant and then creped to about 30%. Its permeability, caliper and conductance were 4103 darcies, 0.028 inches and 146 darcies/mil respectively. Another cover (Cover 16) was a 0.5 osy (17 gsm) polypropylene spunbond web with 2.2 denier fibers having 0.3 weight percent AHCOVEL surfactant. It had a permeability of about 645 darcies, a caliper of 0.009 inches and a conductance of about 70. Cover 16 was not creped and was used as a control for testing Covers 14 and 15. The TEWL test results are given in Table 7 and show positive results versus the uncreped control cover.

TABLE 7

| Specimen | Conductance | TEWL | TEWL reduction | % TEWL reduction |
|---|---|---|---|---|
| Cover 16 | 70 | 43.25 | NA | NA |
| Cover 15 | 188 | 33.75 | −9.5 | −22 |
| Cover 14 | 146 | 36.11 | −7.1 | −16.5 |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. A three dimensional material comprising an adhesively creped microfiber web having an upper and a lower surface, each having a surface energy, wherein said material has a $f_i(\psi)$ of less than 0.87, a SA/VV of less than 186 $cm^2/cm^3$, and a caliper of less than 0.150 inches and wherein an average pore size for a first volume encompassing a top surface is not the same as an average pore size for a second volume encompassing a lower surface.

2. The material of claim 1 wherein at least a portion of said fibers is wettable.

3. The diaper of claim 2 further comprising a hydrophobic web of fibers adjacent said material as a liner.

4. The diaper of claim 3 wherein said material is oriented in said diaper such that a side away from a wearer is hydrophobic as a liner.

5. The diaper of claim 3 wherein said material is oriented in said diaper such that a side toward a wearer is hydrophobic as a liner.

6. The material of claim 1 further comprising regions of stability which are defined by an intersection of one or more fibers which create deformed, discontinuous, bonded regions.

7. The material of claim 6 wherein said at least a portion of said fibers is wettable.

8. The material of claim 1 wherein said fibers are selected from the group consisting of natural fibers, synthetic fibers, and blends thereof and said synthetic fibers are made from a polymer selected from the group consisting of polyesters, polyamides, acrylics, polyolefins, plastomers, elastomers, and blends thereof.

9. The material of claim 8 wherein said polyolefin is selected from the group consisting of polyethylene, polypropylene, polybutylene and copolymers and blends thereof.

10. The material of claim 1 having a Z-direction permeability greater than 2000 darcies.

11. The material of claim 1 wherein the surface energy of the lower surface is higher than the surface energy of the upper surface.

12. A diaper comprising the material of claim 1 as a liner.

13. The diaper of claim 12 which further comprises a breathable outercover as a liner.

14. A training pant comprising the material of claim 1 as a liner.

15. An incontinence product comprising the material of claim 1.

16. A bandage comprising the material of claim 1.

17. A sanitary napkin comprising the material of claim 1 as a liner.

18. A topsheet for personal care products comprising the material of claim 1 wherein at least some of the fibers are wettable.

19. A diaper comprising the material of claim 18.

20. The diaper of claim 18 further comprising a hydrophobic web of fibers adjacent said material.

21. The diaper of claim 20 wherein said material is oriented in said diaper such that a side away from the wearer is hydrophobic.

22. The diaper of claim 20 wherein said material is oriented in said diaper such that a side toward a wearer is hydrophobic.

23. The diaper of claim 19 which further comprises a breathable outercover.

24. A training pant comprising the material of claim 18 as a liner.

25. An incontinence product comprising the material of claim 18.

26. A bandage comprising the material of claim 18.

27. A sanitary napkin comprising the material of claim 18 as a liner.

28. The topsheet of claim 27 having an intake time for menses simulant of less than 20 seconds according to the rate block intake test.

29. The topsheet of claim 27 having a rewet less than 0.30 grams as measured using the rewet test.

30. The topsheet of claim 27 having an average stain size less than 700 mm$^2$ as measured using the fluid retention/stain test.

31. The topsheet of claim 27 having average fluid retention less than 0.040 grams as measured using the fluid retention/stain test.

* * * * *